United States Patent [19]

Nagasawa et al.

[11] 3,936,452

[45] Feb. 3, 1976

[54] PROCESS OF PRODUCING PYRIMIDYL THIOCARBONATES

[75] Inventors: Takeshi Nagasawa; Katumasa Kuroiwa; Kouichi Narita, all of Koriyama, Japan

[73] Assignee: Nitto Boseki Co., Ltd., Fukushima, Japan

[22] Filed: June 13, 1974

[21] Appl. No.: 479,189

Related U.S. Application Data

[62] Division of Ser. No. 287,410, Sept. 8, 1972, Pat. No. 3,852,290.

[52] U.S. Cl............................................. 260/251 R
[51] Int. Cl.².................................... C07D 239/10
[58] Field of Search .................... 260/455 B, 251 R

[56] References Cited
UNITED STATES PATENTS

| 2,923,727 | 2/1960 | Neumoyer....................... 260/455 B |
| 3,359,296 | 12/1967 | Newallis et al.................. 260/455 B |
| 3,789,061 | 1/1974 | Hoyer et al. ..................... 260/455 B |
| 3,855,238 | 12/1974 | Batesky et al.................... 260/455 B |

OTHER PUBLICATIONS
(Houben-Weyl), "Methoden Der Organischen Chemie", p. 808, (1955).

*Primary Examiner*—Lewis Gotts
*Assistant Examiner*—D. R. Phillips
*Attorney, Agent, or Firm*—Karl W. Flocks

[57] ABSTRACT

Thiolcarbonates represented by the formula,

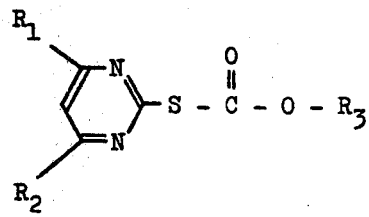

wherein $R_1$ and $R_2$ are individually a hydrogen atom or a methyl group, and $R_3$ is a straight chain or branched chain saturated or unsaturated alkyl group having 1 to 5 carbon atoms or is a benzyl or benzhydryl group which may be nuclear substituted, are easily produced by reacting an alkali metal salt of 2-mercaptopyrimidine with phosgene, and reacting the resulting thiolchloroformate with an alcohol ($R_3$OH).

9 Claims, 22 Drawing Figures

PROCESS OF PRODUCING PYRIMIDYL THIOCARBONATES

This is a division of application Ser. No. 287,410, filed Sept. 8, 1972 now U.S. Pat. No. 3,852,290, 12/3/74.

This invention relates to the preparation of novel thiolcarbonates.

Amines and hydrazines having protected amino and/or protected peptides, are quite useful compounds as starting materials for synthesis of various peptides which are extremely useful as foods and pharmaceuticals, or for synthesis of other compounds.

Recently, it has come to be widely recognized that in the synthesis of N-protected amino acids and N-protected peptides, t-alkyloxycarbonyl groups such as t-butyloxycarbonyl and t-amyloxycarbonyl groups; benzhydoxycarbonyl groups; and nuclear substituted or unsubstituted benzyloxycarbonyl groups such as benzyloxycarbonyl, p-methoxybenzyloxycarbonyl, p-nitrobenzyloxycarbonyl, p-chlorobenzyloxycarbonyl and p-bromobenzyloxycarbonyl groups are useful as protective groups for amino and/or imino groups of amines and hydrazines, particularly amino acids and peptides. Among these protective groups, the t-alkyloxycarbonyl groups are easily cut from the protected amino or imino groups by means of acids but are stable to catalytic reduction, whereas the benzyloxycarbonyl group is stable to acids but is easily cut by catalytic reduction. Taking advantage of such differences in stability between protective groups, the synthesis of complex peptides has extensively been conducted selectively. Further, a peptide synthesis method called solid-phase method has recently been developed by R. B. Merrifield [Journal of Amercian Chemical Society, 85, 2149 (1963)]. Amino acids, which have the above-mentioned t-alkyloxycarbonyl groups or nuclear substituted or unsubstituted benzyloxycarbonyl groups as protective groups, have come to be used also as starting components in said solid-phase method, and the importance thereof has come increasingly greater.

As acylating agents for preparation of such N-protected amines and hydrazines, various compounds have heretofore been proposed. For example, t-alkyl p-nitrophenyl carbonates [Journal of American Chemical Society, 79, 6180 (1957); Chemische Berichte 95, 1 (1962)], t-alkyl N-hydroxysuccinimidyl carbonates [Tetrahydron Letters, 39, 4765 (1966)], t-alkyl 8-hydroxyquinolyl carbonate [Liebigs Annalen der Chemie, 716, 216 (1968)], t-alkyl 2,4,5-trichlorophenyl carbonates [Journal of Chemical Society (C), 2632 (1967); Liebigs Annalen der Chemie, 724, 204 (1969)], t-alkyl pentachlorophenyl carbonates [Japanese Patent Publication Nos. 19,685/70 and 36,729/70], t-alkyloxycarbonyl azides [Journal of American Chemical Society, 79, 442 (1957), 81, 955 (1959), 82, 2725 (1960); Bulletin of the Chemical Society of Japan, 37, 591 (1964); Liebigs Annalen der Chemie, 702, 188 (1967)], t-alkylcyanoformates [Journal of Organic Chemistry, 29, 2820 (1964)], t-alkylchloroformates [Japanese Patent Publication No. 10/71; Bulletin of the Chemical Society of Japan, 38, 1522 (1965)] and t-alkylfluoroformates [Japanese Patent Publication No. 22,729/70] have been known as t-alkyloxycarbonylating agents, and benzyl N-hydroxypiperidyl carbonates [Chemical and Industry 1722 (1966)], p-methoxybenzylazide formates [Chemische Berichte, 95, 1 (1962)] and 2,4,5-trichlorophenoxycarbonates [Liebigs Annalen der Chemie 724, 204 (1969)] have been known as aralkyloxycarbonylating agents.

However, the above-mentioned known alkyloxycarbonylating agents and aralkyloxycarbonylating agents (hereinafter, these are inclusiveley referred to as "acylating agents") have many such drawbacks as mentioned below.

Starting materials for synthesis of the acylating agents are expensive; operations for synthesis thereof are complex and require a long period of time, a high temperature and the like severe conditions; and the resulting acylating agents themselves are unstable. Operations for acylating amines and hydrazines by use of the above-mentioned acylating agents are complex, require a long period of time, a high temperature and the like severe conditions; the conversion of acylation is low; the acylating agents have such selectivity as to react with only specific amines and hydrazines; the acylation products are difficultly purified; and, in case amines and hydrazines to be acylated have other active groups in addition to amino and/or amino groups, the said other groups should have previously been protected. Despite the fact that in such acylation, particularly in the acylation of amino acids and peptides, the purification of acylation products is an extremely important question, the above-mentioned known acylating agents, particularly mixed carbonates of phenols, have such great drawback that phenols, which are released with progress of the reaction, tend to migrate in the acylation products and the removal of migrated phenols is extremely difficult. The azide type acylating agents are explosive, in general, and hence should be stored, handled and reacted under strictly controlled conditions. Further, the benzyl- and t-alkyl-chloroformates, which may nuclear substituted, have such drawback that in case amines or hydrazides to be treated, e.g. amino acids, have other active groups in addition to amino and/or imino groups to be acylated, i.e. in case the amino acids are, for example, serine or threonin having hydroxyl groups, cystein having mercapto groups, and histidine having imidazole groups, the above-mentioned chloroformates react not only with the amino and/or imino groups but also with the said other active groups, so that the active groups other than the amino and/or imino groups to be acylated would have previously been protected by other protective groups.

With an aim to overcome the various drawbacks of the known acylating agents, the present inventors made extensive studies with respect to the functions and production processes of pyrimidyl thiolcarbonate to find that the aforesaid thiolcarbonates are suitable for various useful applications and have markedly excellent functions as acylating agents for introducing N-protective groups into amines and hydrazines, particularly amino acids and peptides, and that the thiolcarbonates can be easily produced on commercial scale. Based on the above finding, the inventors have accomplished the present invention.

The above-mentioned thiolcarbonates are novel compounds, and processes for acylating amines are hydrazines by use of such novel compounds have not been proposed yet.

An object of the invention is to provide a process for producing the novel thiolcarbonates.

Other objects and advantages of the present invention will become apparent from the description made hereinbelow.

The novel thiolcarbonates according to the present invention are represented by the formula,

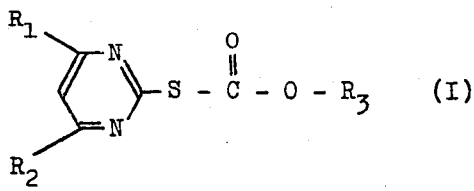

wherein $R_1$ and $R_2$ are individually a hydrogen atom or a methyl group; and $R_3$ is a straight chain or branched chain saturated or unsaturated alkyl group having 1 to 5 carbon atoms, or a benzyl or benzhydryl group

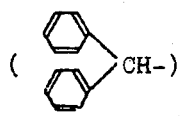

which may be nuclear substituted.

In the above, the alkyl group includes, for example, methyl, ethyl, propyl, isopropyl, allyl, butyl, t-butyl, amyl and t-amyl groups, and the benzyl group which may be nuclear substituted includes, for example, benzyl, p-methoxybenzyl, 2,4-dimethoxybenzyl, 2,4,6-trimethoxybenzyl p-nitrobenzyl, p-chlorobenzyl and p-bromobenzyl groups.

Some examples of the compounds represented by the formula (I) are methyl pyrimidyl-2-thiolcarbonate, methyl 4-methyl-pyrimidyl-2-thiolcarbonate and methyl 4,6-dimethyl-pyrimidyl-2-thiolcarbonate; and ethyl pyrimidiyl-2-thiolcarbonate, propyl pyrimidyl-2-thiolcarbonate, isopropyl pyrimidyl-2-thiolcarbonate, allyl pyrimidyl-2-thiolcarbonate, n-butyl pyrimidyl-2-thiolcarbonate, t-butyl pyrimidyl-2-thiolcarbonate, n-amyl pyrimidyl-2-thiolcarbonate, t-amyl pyrimidyl-2-thiolcarbonate, benzyl pyrimidyl-2-thiolcarbonate, p-methoxybenzyl pyrimidyl-2-thiolcarbonate, 2,4-dimethoxybenzyl pyrimidyl-2-thiolcarbonate, 2,4,6-trimethoxybenzyl pyrimidyl-2-thiolcarbonate, p-nitrobenzyl pyrimidyl-2-thiolcarbonate, p-chlorobenzyl pyrimidyl-2-thiolcarbonate p-bromobenzyl pyrimidyl-2-thiolcarbonate and benzhydryl pyrimidyl-2-thiolcarbonate (in which thiolcarbonates having 4-methyl and 4,6-dimethyl substituents in the pyrimidyl rings have been omitted, but these are naturally included in the compounds of the present invention).

Among the thiolcarbonates represented by the formula (I), the t-alkyl type, nuclear substituted or unsubstituted benzyl type and benzhydryl type carbonates are particualarly important as acylating agents for use in the synthesis of N-protected amino acids and N-substituted peptides. Typical examples of such thiolcarbonates are t-butyl pyrimidyl-2-thiolcarbonate, t-butyl 4-methyl-pyrimidyl-2-thiolcarbonate and t-butyl 4,6-dimethyl-pyrimidyl-2-thiolcarbonate; and t-amyl pyrimidyl-2-thiolcarbonate, benzyl pyrimidyl-2-thiolcarbonate, p-methoxybenzyl pyrimidyl-2-thiolcarbonate, 2,4-dimethoxybenzyl pyrimidyl-2-thiolcarbonate, 2,4,6-trimethoxybenzyl pyrimidyl-2-thiolcarbonate, p-nitrobenzyl pyrimidyl-2-thiolcarbonate, p-chlorobenzyl pyrimidyl-2-thiolcarbonate, p-bromobenzyl pyrimidyl-2-thiolcarbonate and benzhydryl pyrimidyl-2-thiolcarbonate (in which thiolcarbonates having 4-methyl and 4,6-dimethyl substituents in the pyrimidyl rings have been omitted, but these are naturally included in the compounds of the present invention.

In the t-alkyl type, nuclear substituted or unsubstituted benzyl type and benzhydryl type thiolcarbonates represented by the formula (I), those having methyl groups at the 4 and 6 positions of a pyrimidyl ring are most preparable since they show moderate activities in aminolysis of amino acids or peptides.

The thiolcarbonates represented by the formula (I) can be easily produced on commercial scale from inexpensive industrial reagents, as will be mentioned later. Further, the thiolcarbonates are stable compounds and hence can be easily stored and handled and, moreover, the thiolester portions thererof are extremely high in activity. Accordingly, they are particularly preferable as acylating agents for compounds having amino and/or imino groups.

The thiolcarbonates represented by the formula (I) can be easily produced on commercial scale according to the below-mentioned process, using as starting materials 2-mercapto-4- and/or 6-methyl-substituted or unsubstituted pyrimidines:

A process carried out by reacting a 2-mercapto-4- and/or 6-methyl-substituted or unsubstituted pyrimidine with an alkali, reacting the resulting alkali metal salt of said pyrimidine with phosgene and then reacting the resulting pyrimidyl thiolchloroformate with an alcohol.

The process is explained in further detail below.

As is clear from the reaction schema shown below, the desired compound (I) is obtained by reacting an alkali metal salt represented by the formula (II) with phosgene, in the absence of water which causes decomposition of the resultant thiolchloroformate and reacting the resulting thiolchloroformate represented by the formula (III) in the presence of a base with an alcohol represented by the formula (IV).

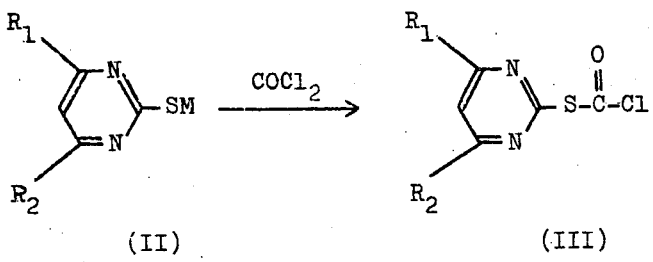

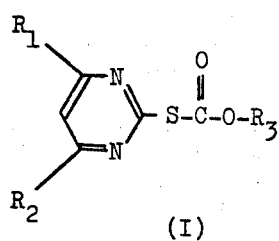

wherein $R_1$, $R_2$ and $R_3$ are as defined in the formula (I), and M is an alkali metal, preferably lithium, sodium or potassium.

In the above-mentioned process, the alkali metal salt represented by the formula (II) is easily formed by dissolving a 2-mercapto-4- and/or 6-methyl-substituted or unsubstituted pyrimidine in an aqueous solution of an alkali metal hydroxide, preferably lithium hydroxide, sodium hydroxide or potassium hydroxide, at a concentration of preferably 10 to 50 % by weight. After the dissolution, the aqueous solution is charged into a large amount of acetone to deposit the said alkali metal salt as a precipitate, which is then recovered by filtration and then dried, for example, at 120°C. under reduced pressure, whereby the alkali metal salt of pyrimidine can be obtained in the form of a powder or mass.

The above-mentioned 2-mercapto-4- and/or 6-methyl-substituted or unsubstituted pyrimidine, e.g. 2-mercapto-pyrimidine or 2-mercapto-4,6-dimethylpyrimidine, can be easily prepared according to a known process from 1,1,3,3-tetraethoxypropane and thiourea or from acetylacetone and thiourea, respectively, in the presence of hydrochloric acid as a catalyst.

The reaction of the alkali metal salt represented by the formula (II) with phosgene is carried out by adding the alkali metal salt (II) to a phosgene solution under cooling, preferably under cooling at −40° to +5°C., and then stirring the resulting mixture at an optional temperature below the reflux temperature of the solvent, preferably at 0° to 40°C. However, the said reaction sufficiently progresses even at about room temperature, and hence is ordinarly effected at a temperature about room temperature (15° to 30°C). The reaction time varies depending on the kind of the alkali metal salt (II) and on the reaction temperature, but is ordinarily from 10 to 120 minutes. The amount of phosgene used is preferably about 1 to 2 moles per mole of the said alkali metal salt (II). This amount, however, is not critical, and phosgene may be used in an amount of more than 2 moles per mole of the alkali metal salt (II). The solvent for phosgene may be any solvent so far as it is inert to the reactants and to the reaction product, and is preferably petroleum ether, ether, benzene, toluene, methylene chloride, xylene, chloroform or tetrahydrofuran, for example.

After completion of the above-mentioned reaction, excess phosgene is removed by a suitable procedure, e.g. by injection of nitrogen at a temperature of 50° to 60°C. Subsequently, the reaction liquid is cooled to room temperature and then filtered, and the filtrate is concentrated under reduced pressure in an inert gas such as nitrogen, whereby a crude pyrimidyl thiolchloroformate in the form of a liquid which is represented by the formula (III) is obtained in a yield of about 80 to 90 %.

The thiolchloroformate represented by the formula (III) is quite easily reactive with water, so that the above-mentioned operation should be effected, both during and after the reaction, in such a state as has sufficiently been freed from water. In a water-free state, the pyrimidyl thiolchloroformate (III) is stable.

The pyrimidyl thiolchloroformate (III) decomposes at a temperature of about 100°C. and hence is difficulty purified by distillation, in general. In the subsequent reaction, therefore, the pyrimidyl thiolchloroformate (III) is ordinarily used in a crude form, and the reaction liquid of pyrimidyl thiolchloroformate prior to concentration is sometimes used as it is. Among the pyrimidyl thiolchloroformates (III), however, 4,6-dimethylpyrimidyl-2-thiolchloroformate can be recovered in the form of crystals at a temperature below about 5°C., and therefore the thus recovered crystals may be subjected to the subsequent reaction.

The reaction of the pyrimidyl thiolchloroformate represented by the formula (III) with the alcohol represented by the formula $R_3$-OH (IV) is carried out by dissolving in an inert solvent the alcohol (IV) and a base as a deacidifying agent, dropping into the resulting solution under cooling, preferably at a temperature of −5° to +5°C., the pyrimidyl thiolchloroformate (III) obtained by the aforesaid reaction, and heating the resulting mixture at a temperature below the reflux temperature of the solvent. This reaction, however, proceeds sufficiently quickly even at about room temperature and hence is ordinarily effected at a temperature about room temperature. The reaction time is ordinarily within the range from 2 to 24 hours.

Examples of the alcohol of the formula (IV) include alkyl alcohols such as methanol, ethanol, n-propanol, iso-propanol, allyl alcohol, n-butanol, t-butanol, amyl alcohol and t-amyl alcohol, and benzyl alcohols and benzhydrols which may have been nuclear substituted such as benzyl alcohol, anise alcohol, 2,4-dimethoxybenzyl alcohol, 2,4,6-trimethoxybenzyl alcohol, p-nitrobenzyl alcohol, p-chlorobenzyl alcohol and p-bromobenzyl alcohol.

As the solvent, any solvent is usable so far as it is inert to the reactants and the reaction product, and ether, benzene, toluene, xylene, methylene chloride, chloroform, petroleum benzene, tetrahydrofuran or other saturated hydrocarbon, for example, is preferable.

As the deacidifying agent, any of those which are ordinarily used in this technical field is usable, and there may be used a tertiary amine such as, for example, triethylamine, N-alkylmorpholine, N,N-dialkylaniline, pyridine or quinoline.

Alternatively, the above reaction may be effected without the use of the above-mentioned solvent, while making the said tertiary amine display the actions of both the solvent and the deacidifying agent. Particularly when t-butanol, t-amyl alcohol or the like tertiary alkyl alcohol, which is great in steric hindrance and low in reactivity, is used in the reaction, it is preferable to adopt the process in which the above-mentioned tertiary amine is used as a solvent.

After completion of the reaction, the precipitate formed is separated by filtration, and the filtrate is washed and dried according to an ordinary procedure. For example, the filtrate is washed with a cold aqueous hydrochloric acid solution and an aqueous solium chloride solution, and then dried over anhydrous sodium sulfate. Thereafter, the solvent is removed by distillation under reduced pressure, whereby the desired thiolcarbonate represented by the formula (I) in the form of crude crystals is obtained in such a high yield as 80 % or more, in general. The thus obtained crude crystals are ordinarily purified by recrystallization from a suitable solvent such as, for example, petroleum ether, a hydrocarbon, ethyl acetate, benzene and water-alcohol mixture. In case a tertiary amine is used as a solvent, it is preferable that the filtrate after separation of precipitate is charged with the said inert solvent and then subjected to the same washing, drying, solvent removal distillation and recrystallization as above, The novel thiolcarbonates represented by the formula (I), which are produced according to the above-mentioned processes, are quite useful for protecting with groups of the formula

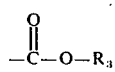

the amino or imino groups of compounds having amino and/or imino groups, e.g. amines, hydrazines, amino acids and peptides, and hence are used as acylating agents for the said compounds.

In the next place, a process for acylating varous amines and hydrazines by using as acylating agents the thiolcarbonates represented by the formula (I) is explained below.

The acylation process according to the present invention comprises reacting the thiolcarbonate of the formula (I) with a compound (VII) having amino and/or imino groups in an inert organic solvent or in an aqueous solution thereof in the presence or absence of a base, as shown by the following reaction schema:

The compound of the formula (VII) includes an univalent amine or imine, and may also be a compound having two or more amino and/or imino groups. In the latter case, when all of the functional groups therein are to be acylated, the compound of the formula (I) is used in an amount corresponding to the numbers of the functional groups in the compound of the formula (VII).

In the above reaction, the inert organic solvent may be any of water-soluble organic solvents which are inert to the reactants and the reaction product, and is preferably t-butyl alcohol, dioxane, tetrahydrofuran or dimethylformamide, for example.

The base may be any of those which are ordinarily used in this technical field, and includes, for example, the tertiary amines and the like organic bases and inorganic bases which are used in the production of thiolcarbonates represented by the formula (I).

Generally, the above-mentioned reaction is carried out at a temperature ranging from 0° to 80°C. Depending on the kind of the compound having an amino or imino group, however, the reaction may be conducted at a temperature below 0°C. or above 80°C. If the temperature is excessively low, the reaction rate becomes extremely low, while if the temperature is excessively high, side-reactions are undesirably brought about, in some cases. However, in case the compound having amino and/or imino groups has other active group in addition thereto, e.g. in case the said compound is any of saccharides or steroids, the reaction is desirably carried out at a temperature below 0°C., particularly below −20°C. When the reaction is carried out at a temperature about room temperature, a reaction time of more than 2 hours is required, in general. However, when the reaction is conducted at such a high temperature as about 60°C., the reaction is sufficiently complete within 2 hours.

After completion of the reaction, the reaction product can be easily purified according to ordinary washing, extraction and recrystallization. Particularly, the 2-mercapto-4- and/or 6-methyl-substituted or unsubstituted pyrimidine liberated in the above reaction is eas-

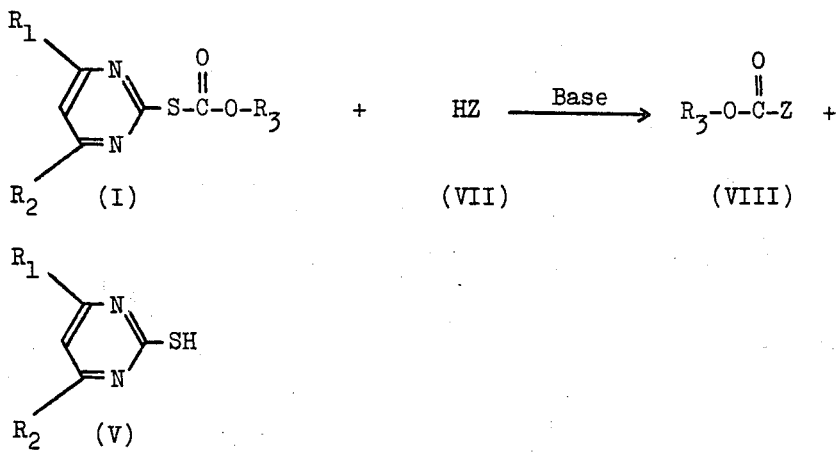

wherein $R_1$, $R_2$ and $R_3$ are as defined in the aforesaid formula (I), and H in the formula (VII) is a hydrogen atom in the amino or imino group of the compound of the formula (VII), and therefore z is a group formed by removing one hydrogen atom from the amino or imino group thereof.

ily soluble in acid or alkali, so that the reaction product can be readily purified by washing with a dilute aqueous acid or alkali solution.

Examples of the compound having amino and/or imino groups, which is represented by the formula (VII), include a wide scope of compounds such as aliphatic, alicyclic, aralkyl, aromatic and heterocyclic primary and secondary amines; hydrazines, and derivatives thereof; amino acids, peptides, and derivatives thereof; various saccharides and steroids having amino and/or imino groups. These amine compounds may contain, in addition to the amino and/or imino groups, other active groups such as, for example, alcoholic and/or phenolic hydroxyl, mercapto, carboxyl, nitro or imidazole groups. However, it is natural that the introduction of acryl groups, particularly t-alkyloxycarbonyl groups, benzhydroxycarbonyl groups, and benzyloxycarbonyl groups, which may have been nuclear substituted, is most important for amino acids and peptides. In the examples shown later, therefore, the acylation of amino acids is explained chiefly, and the acylation of amines and hydrazines is explained with respect only to typical compounds. It will be understood from the above explanation and from the explanation made in the examples that the acylating agents of the present invention are concerned with the amino and/or imino groups of the compounds to be acylated and have nothing to do with the matrix structures of the compounds to be aminolyzed therewith. When the acylating agents of the present invention are used, any compounds having amino and/or imino groups can be acylated to give acylation products in high yields. Some examples of such compounds are as shown below.

As amino acids and derivatives thereof, there are used all the amino acids of natural occurrence and derivatives thereof. Concretely, these compounds include, for example, α-amino acids such as alanine (Ala), arginine (Arg), aspartic acid (Asp), asparagine (Asn), cysteine (Cys), cystine [(Cys)$_2$], diiodotyrosine [Tyr (I$_2$)], glutamic acid (Glu), glycine (Gly), histidine (His), hydroxyproline (Hyp), isoleucine (Ile), leucine (Leu), lysine (Lys), methionine (Met), norleucine (Nle), ornithine (Orn), phenylalanine (Phe), proline (Pro), serine (Ser), threonine (Thr), tryptophan (Trp), tyrosine (Tyr) and valine (Val); β- and ω-amino acids such as β-alanine, γ-aminobutyric acid and ε-aminocaproic acid; salts of said amino acids such as sodium, potassium and magnesium salts; and derivatives of said acids such as acid esters and acid amides. Further, synthetic and semi-synthetic amino acids such as α-methylalanine may also be used. It is natural that N-terminal-free peptides obtained from two or more of the said amino acids are also usable.

As amines and hydrazines other than the abovementioned amino acids, there may be shown, for example, aliphatic and alicyclic primary and secondary amines such as methylamine, dimethylamine, ethylamine, 2-phenylethylamine, ethanolamine, isopropylamine, tertiary butylamine, N-ethyl-N-β-hydroxyethylamine, octylamine, laurylamine and cyclohexylamine; primary and secondary aralkylamines and nuclear substituted derivatives thereof such as benzylamine, N-methylbenzylamine, p-nitrobenzylamine p-chlorobenzylamine and 2-phenylethylamine; aromatic primary and secondary amines and nucleas substituted derivatives thereof such as aniline, N-methylaniline, toluidine, xylidine, p-aminophenol, p-methylaminophenol, o-carbomethylaniline, p-phenetidine, diphenylamine, α- (and β-) naphthlamines and 4-aminonaphthol (1); heterocyclic primary and secondary amines such a ethyleneimine, pyrrolidine, pyrazole and indole, and nuclear substituted derivatives thereof; and hydrazines and derivatives thereof such as hydrazine, phenylhydrazine, 2,4-dinitrophenylhydrazine and N-methyl-N-phenylhydrazine.

As the saccharides and steroids, there may be used various saccharides and steroids having amino and/or imino groups such as 2-amino-1,6-anhydro-2-deoxy-β-D-glucopyranose, L-glucosamine and methyl-3-amino-β-L-xylopyranoside. In the acylation of these saccharides and steroids, particularly in the cases where they have other active groups in addition to amino or imino groups, it is required in most cases that only the amino or imino groups should be selectively acylated. When the acylating agents of the present invention is used, only the amino or imino groups can be selectively acylated even if said other active groups have not been protected at all.

In the acylation process according to the present invention, a compound having amino and/or imino groups is subjected to acylation reaction in the form of a free amine or of a salt thereof such as, for example, hydrochloride, hydrobromide, hydroiodide, sulfate or sulfite. In case the compound is subjected to the reaction in the form of a salt, the aforesaid deacidifying agent is required to be added to the reaction system.

According to the acylation process, in which the thiolcarbonate represented by the formula (I) is used as an acylating agent, the above-mentioned compound having amino and/or imino groups can be easily acylated under mild conditions to give a corresponding acylation product in such a high yield as more than about 90 %, in general. The acylating agent of the present invention is well reactive with substantially all amine compounds. Further, the acylating agent of the present invention has such characteristic actions which are not seen in the conventional acylating agents that even though a compound having amino and/or imino groups, which is to be reacted therewith, additionally has in the molecule such active group as, for example, an alcoholic or phenolic hydroxyl, mercapto, carboxyl or imidazole group, the acylating agent reacts selectively with only the amino and/or imino groups.

The use of the acylating agent of the present invention brings about such advantage that the acylation product obtained by use of said acylating agent can be purified with extreme ease. That is, in the aminolysis of the thiolcarbonate represented by the formula (I) by means of amino and/or imino groups, there are such characteristics that the 2-mercapto-4- and/or 6-methyl-substituted or unsubstituted pyrimidine is liberated with the progress of the reaction and that the said mercapto-pyrimidine is an amphoteric compound and is easily soluble in acid or alkali, so that it can be easily removed by washing said solution phase with a dilute aqueous acid or alkali solution, with the result that an extremely high purity acylation product can be obtained. In some cases, the produced mercapto-pyrimidine is precipitated with the progress of the reaction. The precipitated mercapto-pyrimidine is filtered off and the filtrate is purified by washing with a dilute acid or alkali solution as mentioned above. The recovered mercapto-pyrimidine can be reused as a starting material for the production of the acylating agent of the present invention.

In the attached drawings.

Figure 1:
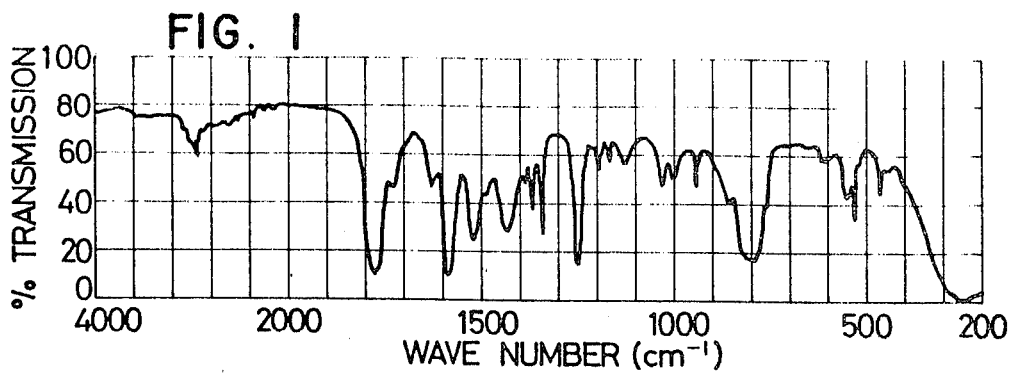
FIG. 1 is the infrared spectrum of 4,6-dimethylpyrimidyl-2-thiolchloroformate, the intermediate for the production of the thiolcarbonates of the formula (I).

Procedures for preparing 2-mercapto-4- and/or 6-methyl-substituted or unsubstituted pyrimidines and thiolchloroformate thereof which are starting materials or intermediates for production of the present thiolcarbonates represented by the formula (I) are explained below with reference to referential examples.

REFERENTIAL EXAMPLE 1

Synthesis of 2-mercapto-pyrimidine:

A solution of 61 g. (0.80 mole) of thiourea in 600 ml. of ethanol was charged into a 2-liter threenecked flask equipped with a stirrer and a reflux condenser, and 200 ml. of concentrated hydrochloric acid was added to the solution, whereby the liquid became homogenous after several minutes. This liquid was mixed with 176 g. (0.80 mole) of 1,1,3,3-tetraethoxypropane, and the resulting mixture was reacted under reflux for about 1 hour. After completion of the reaction, the reaction liquid was cooled to 10°C. in an ice bath and maintained at said temperature for 30 minutes to deposit 2-mercapto-pyrimidine hydrochloride in the form of yellow crystals. The crystals were collected in a Buchner funnel, washed with 100 ml. of cold alcohol and then dried at room temperature to obtain 89 g. of crude 2-mercapto-pyrimidine hydrochloride in yield of 75 %.

25 Grams (0.17 mole) of the above-mentioned crude 2-mercapto-pyrimidine hydrochloride was suspended in 50 ml. of water, and the resulting suspension was adjusted to pH 7 to 8 by addition of 27 ml. of a 20 % aqueous sodium hydroxide solution, whereby 2-mercaptopyrimidine was precipitated. This mercaptopyrimidine was recovered by filtration with a Buchner funnel, washed with 50 ml. of cold water and then recrystallized from a solution comprising 300 ml. of water and 300 ml. of ethanol to obtain 19 g. of 2-mercapto-pyrimidine in yield of 70 %.

Elementary analysis: Calcd. C: 42.84 %, H: 3.59 %, N: 24.98 %, S: 28.59 % (for $C_4H_4N_2S$); Found: C: 42.91 %, H: 3.68 %, N: 24.92 %, S: 28.48 %.

REFERENTIAL EXAMPLE 2

Synthesis of 2-mercapto-4,6-dimethyl-pyrimidine:

76 Grams (1.0 mole) of thiourea was suspended in a solution of 120 g. (1.2 moles) of acetylacetone in 2,500 ml. of ethanol. The resulting suspension was mixed with 250 ml. of concentrated hydrochloric acid, and then reacted under reflux for 2 hours. After completion of the reaction, the reaction liquid was cooled, whereby beautiful yellow needle-like crystals of 2-mercapto-4,6-dimethyl-pyrimidine hydrochloride were formed. The reaction liquid was allowed to stand overnight to sufficiently deposit the crystals, which were then recovered by filtration and dried to obtain 140 g. of 2-mercapto-4,6-dimethyl-pyrimidine hydrochloride in yield of 80 %.

To the filtrate after recovery of the abovementioned pyrimidine hydrochloride were again added 110 g. of acetylacetone, 76 g. of thiourea, 100 ml. of ethanol and 150 ml. of concentrated hydrochloric acid, and the resulting mixture was subjected to filtration and drying to obtain 158 g. of 2-mercapto-4,6-dimethylpyrimidine hydrochloride in yield of 90 %. The filtrate in this case was again subjected to the same operation as above to obtain 148 g. of 2-mercapto-4,6-dimethylpyrimidine hydrochloride in yield of 84 %.

200 Grams (1.13 moles) of the above-mentioned 2-mercapto-4,6-dimethyl-pyrimidine hydrochloride was suspended in 400 ml. of water, and the resulting suspension was heated to about 40°C. while gradually adding thereto 70 ml. of a 20 % aqueous sodium hydroxide solution, whereby the 2-mercapto-4,6-dimethyl-pyrimidine hydrochloride was completely dissolved. This solution was adjusted to pH 4.5 to 5.0 by gradual addition of a 20 % aqueous sodium hydroxide solution, whereby pale yellow crystals of 2-mercapto-4,6-dimethyl-pyrimidine were precipitated. The reaction liquid was allowed to stand overnight at room temperature to sufficiently deposit the crystals, which were then recovered by filtration and dried to obtain 117 g. of 2-mercapto-4,6-dimethyl-pyrimidine in yield of 74.3 %.

Elementary analysis: Calcd.: C: 51.40 %, H: 5.75 %, N: 19.98 %, S: 22.87 % (for $C_6H_8N_2S$); Found: C: 51.52 %, H: 5.75 %, N: 20.03 %, S: 22.75 %.

REFERENTIAL EXAMPLE 3

Synthesis of 4,6-dimethyl-pyrimidyl-2-thiolchloroformate:

A solution of 128 g. (3.2 moles) of sodium hydroxide in 600 ml. of water was mixed with 420 g. (3 moles) of 2-mercapto-4,6-dimethyl-pyrimidine, and the resulting mixture was heated to completely dissolve the dimethyl-pyrimidine and then allowed to cool. The resulting solution was charged into 15 liters of acetone, whereby a sodium salt of 2-mercapto-4,6-dimethyl-pyrimidine was precipitated. The precipitated sodium salt was recovered by filtration and then dried at 120°C. for 24 hours to obtain 462 g. of said sodium salt in a solid form in yield of 95 %.

Subsequently, 324 g. (2 moles) of the above-mentioned sodium salt of 2-mercapto-4,6-dimethyl-pyrimidine was added as it was, i.e. in the form of solid, at 0° to 5°C. to 990 g. of a 30 % toluene solution of phosgene, and the resulting mixture was reacted with stirring at room temperature for 1 hour. After completion of the reaction, excess phosgene was removed by distillation at 50° to 60°C., while injecting nitrogen into the reaction liquid. Thereafter, the precipitate formed was filtered and then the toluene was removed by distillation under reduced pressure to obtain about 365 g. of 4,6-dimethylpyrimidyl-2-thiolchloroformate in yield of 90 %.

The thus obtained pyrimidyl-2-thiolchloroformate is hydrolyzed within a short period of time when allowed to stand in air, and hence should be stored in a water-free state. Further, the said pyrimidyl-2-thiolchloroformate is decomposed when heated to above 100°C., and therefore the purification thereof according to distillation was substantially impossible.

Infrared absorption spectrum of the above-mentioned 4,6-dimethyl-pyrimidyl-2-thiolchloroformate is shown in FIG. 1. According to the said drawing, specific absorptions derived from C = 0 in the group of

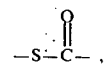

Cl in the group of 1

and pyrimidine ring of said compound are obviously recognized at 1775 cm$^{-1}$, 800 cm$^{-1}$ and 1587 cm$^{-1}$ and 1253 cm$^{-1}$, respectively.

Procedures for producing the present thiolcarbonates represented by the formula (I) are illustrated below with reference to examples.

EXAMPLE 1

Synthesis of ethyl 4,6-dimethyl-pyrimidyl-2-thiolcarbonate:

20.3 Grams (0.44 mole) of dehydrated ethanol and 41.8 g. (0.528 mole) of pyridine were added to 650 ml. of ether. Into the resulting mixture was dropped under stirring and cooling to −5° to 0°C. 81.0 g. (0.40 mole) of the 4,6-dimethyl-pyrimidyl-2-thiolchloroformate obtained in Referential Example 3, and then the mixture was reacted at 20°C. for 3 hours. After completion of the reaction, the reaction liquid was washed twice each with 100 ml. of a 10 % aqueous citric acid solution and 100 ml. of a saturated aqueous sodium chloride solution, and successively dried over anhydrous sodium sulfate and then the ether was removed by distillation to obtain 78.0 g. of ethyl 4,6-dimethyl-pyrimidyl-2-thiolcarbonate in the form of syrup in yield of 92 %. When recrystallized from an ether-petroleum ether solvent, the product showed a melting point of 25°C.

Elementary analysis: Calcd.: C: 50.93 %, H: 5.70 %, N: 13.20 % (for $C_9H_{12}O_2N_2S$); Found: C: 50.92 %, H: 5.69 %, N: 13.23 %.

Figure 2:
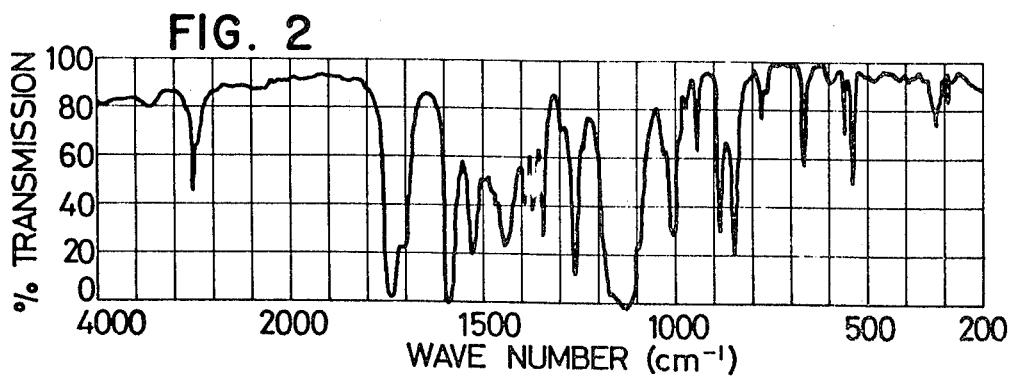
FIG. 2 – FIG. 7 are the infrared spectra of the thiolcarbonates of the formula (I).

FIG. 2 shows the infrared spectrum of ethyl 4,6-dimethyl-pyrimidyl-2-thiolcarbonate. The infrared spectrum shows the presence of

in the ester bond (1735 cm$^{-1}$),

(1125 cm$^{-1}$), the pyrimidine ring (1586 and 1258 cm$^{-1}$), and —CH$_2$—and —CH$_3$ groups (1440 and 1370 cm$^{-1}$).

EXAMPLE 2

Synthesis of t-butyl 4,6-dimethyl-pyrimidyl-2-thiolcarbonate:

Into a solution of 69.7 g. (0.94 mole) of t-butyl alcohol in 185.9 g. of pyridine was dropped under stirring and cooling to −5° to 0°C. 95 g. (0.47 mole) of the 4,6-dimethyl-pyrimidyl-2-thiolchloroformate obtained in Referential Example 3, and the resulting mixture was reacted at 20° to 25°C. for 3 hours. After the reaction, deposited pyridine hydrochloride was separated by filtration, and the filtrate was charged with 500 ml. of water and then extracted 3 times each with 200 ml. of petroleum ether. The petroleum ether phase was sufficiently washed with a cold 1N aqueous hydrochloric acid solution, washed twice with an aqueous sodium chloride solution and dried over anhydrous sodium sulfate, and then the petroleum ether was removed by distillation under reduced pressure, whereby crystals were obtained. The crystals were washed with a small amount of cold n-pentane and then dried to obtain 96 g. of t-butyl 4,6-dimethyl-pyrimidyl-2-thiolcarbonate, yield 85 %, m.p. 50°– 51°C.

Elementary analysis: Calcd.: C: 54.98 %, H: 6.71 %, N: 11.66 %, S: 13.34 % (for $C_{11}H_{16}O_2N_2S$); Found: C: 54.88 %, H: 6.64 %, N: 11.57 %, S: 13.29 %.

Figure 3:
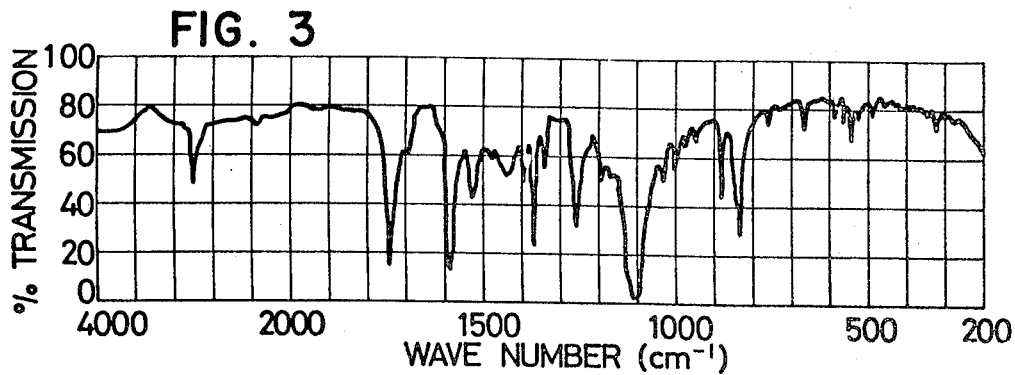

FIG. 3 shows the infrared spectrum of t-butyl 4,6-dimethyl-pyrimidyl-2-thiolcarbonate. The infrared spectrum shows the presence of

in the ester bond (1743 cm$^{-1}$),

(1105 cm$^{-1}$), the pyrimidine ring (1587 and 1258 cm$^{-1}$), and the deformation vibration of CH in —C(CH$_3$)$_3$ (1393 and 1370 cm$^{-1}$).

EXAMPLE 3

Synthesis of t-amyl 4,6-dimethyl-pyrimidyl-2-thiolcarbonate:

Into a solution of 26.4 g. (0.30 mole) of t-amyl alcohol in 61 ml. of pyridine was dropped under stirring and cooling to −5° to 0°C. 30.4 g. (0.15 mole) of the 4,6-dimethyl-pyrimidyl-2-thiolchloroformate obtained in Referential Example 3, and the resulting mixture was reacted at 20° to 25°C. for 3 hours. After the reaction, deposited pyridine hydrochloride was separated by filtration, and the filtrate was charged with 150 ml. of water and then extracted 3 times each with 60 ml. of petroleum ether. The petroleum ether phase was sufficiently washed with a cold 1N aqueous hydrochloric acid solution, washed twice with an aqueous sodium chloride solution and dried over anhydrous sodium sulfate, and then the petroleum ether was removed by distillation under reduced pressure to obtain 33.0 g. of t-amyl 4,6-dimethylpyrimidyl-2-thiolcarbonate in the form of syrup, yield 85 %.

Elementary analysis: Calcd.: C: 56.67 %, H: 7.13 %, N: 11.01 % (for $C_{12}H_{18}O_2N_2S$); Found: C: 56.70 %, H: 7.11 %, N: 11.03 %.

Figure 4:
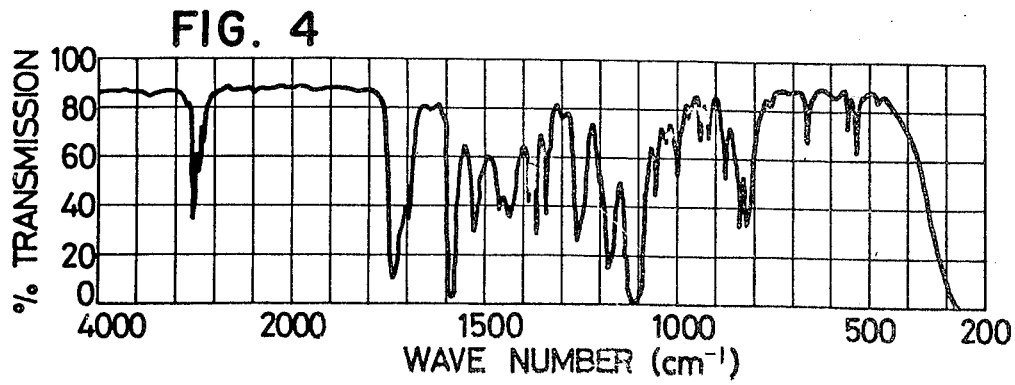

FIG. 4 shows the infrared spectrum of t-amyl 4,6-dimethyl-pyrimidyl-2-thiolcarbonate. The infrared spectrum shows the presence of

in the ester bond (1730 cm$^{-1}$),

(1112 cm⁻¹), the pyrimidine ring (1584 and 1259 cm⁻¹), and —CH₂— and —CH₃ groups (1434 and 1368 cm⁻¹).

EXAMPLE 4

Synthesis of n-butyl 4,6-dimethyl-pyrimidyl-2-thiolcarbonate:

0.44 Mole of n-butanol and 0.528 mole of pyridine were added to 650 ml. of ether. Into the resulting mixture was dropped under stirring and cooling to —5° to 0°C. 0.40 mole of the 4,6-dimethyl-pyrimidyl-2-thiolchloroformate obtained in Referential Example 3, and the mixture was reacted in the same manner as in Example 1. After the reaction, the reaction liquid was washed and dried in the same manner as in Example 1, and then the solvent was removed by distillation to obtain n-butyl 4,6-dimethyl-primidyl-2-thiolcarbonate in a high yield.

EXAMPLE 5

Synthesis of benzyl 4,6-dimethyl-pyrimidyl-2thiolcarbonate:

4.86 Grams (0.045 mole) of benzyl alcohol and 3.57 g. (0.045 mole) of pyridine were dissolved in 100 ml. of methylene chloride. Into the resulting solution was dropped under stirring and cooling to —5° to 0°C. 8.10 g. (0.040 mole) of the 4,6-dimethyl-pyrimidyl-2-thiolchloroformate obtained in Referential Example 3, and the resulting mixture was reacted at room temperature for 3 hours. After completion of the reaction, the reaction liquid was successively washed twice with each 20 ml. of a 10 % aqueous sodium chloride solution, a saturated aqueous sodium bicarbonate solution, a 10 % aqueous sodium chloride solution, a 0.5 N aqueous hydrochloric acid solution and a 10 % aqueous sodium chloride solution, and then dried over anhydrous sodium sulfate. Subsequently, the methylene chloride was removed by distillation, and the residue was recrystallized from an ether-petroleum ether solvent to obtain 11.2 g. of benzyl 4,6-dimethyl-pyrimidyl-2-thiolcarbonate, yield 91.5 %, m.p. 93.4 –94.5° C.

Elementary analysis: Calcd.: C: 61.29 %, H: 5.14 %, N: 10.21 %, S: 11.69 % (for C₁₄H₁₄O₂N₂S);
Found: C: 61.12 %, H: 5.20 %, N: 10.40 %, S: 11.98 %.

Figure 5:
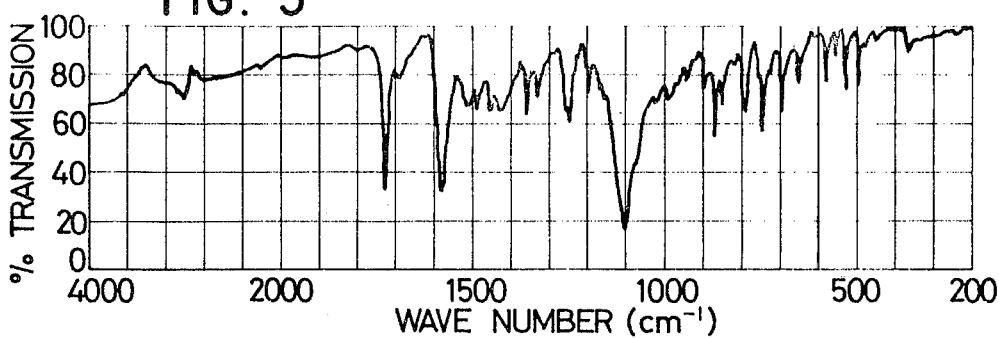

FIG. 5 shows the infrared spectrum of benzyl 4,6-dimethyl-pyrimidyl-2-thiolcarbonate. The infrared spectrum shows the presence of

in the ester bond (1730 cm⁻¹),

(1107 cm⁻¹), the pyrimidine ring (1584 cm⁻¹) and mono-substituted phenyl group (753 and 700 cm⁻¹).

EXAMPLE 6

Synthesis of p-methoxybenzyl 4,6-dimethyl-pyrimidyl-2-thiolcarbonate:

61 Grams (0.44 mole) of anise alcohol and 41.8 g. (0.528 mole) of pyridine were dissolved in 650 ml. of ether. Into the resulting solution was dropped under stirring and cooling to —5° to 0°C. 81.0 g. (0.40 mole) of the 4,6-dimethyl-pyrimidyl-2-thiolchloroformate obtained in Referential Example 3, and the resulting mixture was reacted at room temperature for 3 hours. After the reaction, the reaction liquid was washed 2 times with a 10 % aqueous citric acid solution and a saturated aqueous sodium chloride solution, and dried over anhydrous sodium sulfate, and then the ether was removed by distillation to obtain 120 g. of white crystals of p-methoxybenzyl, 4,6-dimethyl-pyrimidyl-2-thiolcarbonate in yield of 90.0 %. When recrystallized from an etherpetroleum ether solvent, the product showed a melting point of 58° to 60°C.

Elementary analysis: Calcd.: C: 59.19 %, H: 5.30 %, N: 9.20 %, S: 10.54 % (for C₁₅H₁₆O₃N₂S); Found: C: 58.98 %, H: 5.31 %, N: 9.22 %, S: 10.48 %.

Figure 6:
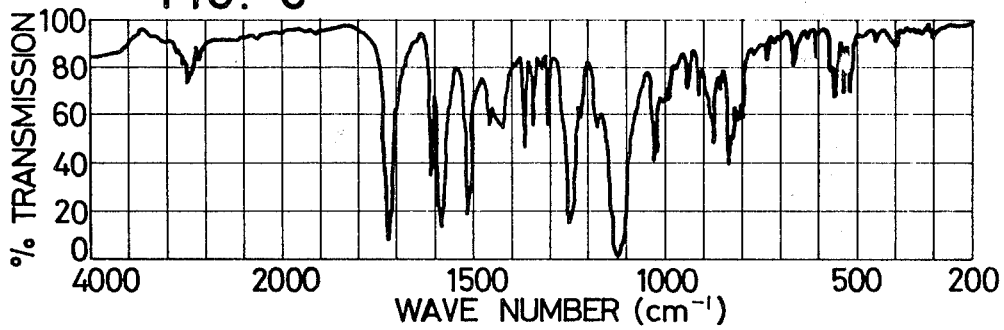

FIG. 6 shows the infrared spectrum of p-methoxybenzyl 4,6-dimethyl-pyrimidyl-2-thiolcarbonate. The infrared spectrum shows the presence of

in the ester bond (1720 cm⁻¹),

(1125 cm⁻¹), the pyrimidine ring (1586 and 1250 cm⁻¹), —O—CH₃ group (2830 cm⁻¹) and 1,4-substituted phenyl group (828 cm⁻¹).

EXAMPLE 7

Synthesis of p-chlorobenzyl 4,6-dimethyl-pyrimidyl-2-thiolcarbonate:

0.44 Mole of p-chlorobenzyl alcohol and 0.528 mole of pyridine were dissolved in 650 ml. of ether. Into the resulting solution was dropped under stirring and cooling to —5° to 0°C. 0.40 mole of the 4,6-dimethylpyrimidyl-2-thiolchloroformate obtained in Referential Example 3, and the resulting mixture was reacted in the same manner as in Example 6. After the reaction, the reaction liquid was washed and dried in the same manner as in Example 6, and then the solvent was removed by distillation to obtain p-chlorobenzyl 4,6-dimethyl-pyrimidyl-2-thiolcarbonate in a high yield.

EXAMPLE 8

Synthesis of p-nitrobenzyl 4,6-dimethyl-pyrimidyl-2-thiolcarbonate:

p-Nitrobenzyl alcohol (0.44 mole) and 0.528 mole of pyridine were dissolved in 650 ml. of ether. Into the resulting solution was dropped under stirring and cooling to —5° to 0°C. 0.40 mole of 4,6-dimethylpyrimidyl-2-thiolchloroformate obtained in Referential Example 3 and the resulting mixture was reacted in the same manner as in Example 6. After the reaction, the reaction liquid was washed and dried in the same manner as in Example 6, and then the solvent was removed by distillation to obtain p-nitrobenzyl 4,6-dimethyl-pyrimidyl-2-thiolcarbonate in a high yield.

EXAMPLE 9

Synthesis of benzlydryl 4,6-dimethyl-pyrimidyl2-thiolcarbonate:

36.85 Grams (0.20 mole) of benzhydrol and 17.40 g. (0.22 mole) of pyridine were dissolved in 450 ml. of ether, and the resulting solution was cooled to −5° to 0°C. Into the solution was dropped a solution of 40.53 g. (0.20 mole) of 4,6-dimethyl-pyrimidyl-2-thiolchloroformate in 50 ml. of ether, and the mixed solution was reacted with the stirring at 20°C. for 4 hours. After the reaction, a pyridine salt form was suction-filtered, and the filtrate was washed twice at 0°C. with 200 ml. of a 5 % aqueous hydrochloric acid solution, once with 200 ml. of a 10 % aqueous sodium bicarbonate solution and once with 200 ml. of a saturated aqueous sodium chloride solution, and dried over anhydrous sodium sulfate, and then the ether was removed by distillation to obtain 50.5 g, of crude crystals of benzhydryl 4,6-dimethyl-pyrimidyl-2-thiolcarbonate in yield of 72 %. When recrystallized from an ethyl acetate-petroleum ether solvent, the product showed a melting point of 99° to 101°C.

Elementary analysis: Calcd.: C: 68.55 %, H: 5.18 %, N: 7.99 %, S: 9.15 % (for $C_{20}H_{18}O_2N_2S$); Found: C: 68.48 %, H: 5.25 %, N: 7.85 %, S: 9.12 %.

Figure 7:
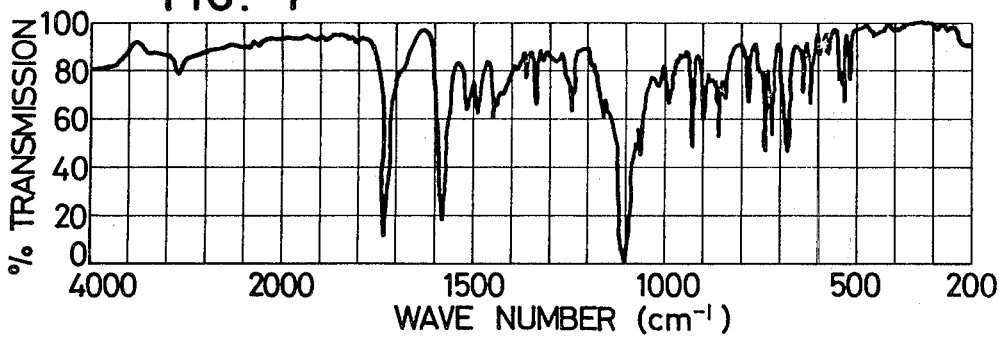

FIG. 7 shows the infrared spectrum benzhydryl 4,6-dimethyl-primidyl-2-thiolcarbonate. The infrared spectrum shows the presence of

in the ester bond (1730 cm$^{-1}$),

(1118 cm$^{-1}$), the pyrimidine ring (1586 cm$^{-1}$) and mono-substituted phenyl group (761 and 700 cm$^{-1}$).

EXAMPLE 10

Synthesis of ethyl 4,6-dimethyl-pyrimidyl-2-thiolcarbonate:

28 Grams (0.2 mole) of 2-mercapto-4,6-dimethyl-pyridine was added to 30 g. of a 50 % aqueous potassium hydroxide solution. Into the resulting mixture was dropped under stirring and ice-cooling a solution of 21.7 g. of ethyl chlorocarbonate in 500 ml. of methylene chloride, and then the mixture was reacted at room temperature for 24 hours. After completion of the reaction, the methylene chloride phase was separated, washed twice with a saturated sodium bicarbonate solution and twice with a 10% aqueous sodium chloride solution, and dried over anhydrous sodium sulfate, and then the methylene chloride was concentrated to obtain 37.5 g. of ethyl 4,6-dimethyl-pyrimidyl-2-thiolcarbonate in the form of syrup in yield of 88.4 %. When recrystallized from an ether-petroleum ether solvent, the product showed a melting point of 23° to 25°C.

Elementary analysis:
Calcd. C: 50.93 %, H: 5.70 %, N: 13.20 % (for $C_9H_{12}O_2N_2S$) Found C: 50.92 %, H: 5.69 %, N: 13.23 %

The infrared spectrum of the thus obtained compound is the same as shown in FIG. 2.

EXAMPLE 11

Synthesis of n-butyl 4,6-dimethyl-pyrimidyl-2-thiolcarbonate:

0.2 Mole of 2-mercapto-4,6-dimethyl-pyrimidine was added to 30 g. of a 50 % aqueous potassium hydroxide solution. Into the resulting mixture was dropped under stirring and ice-cooling a solution of 0.2 mole of n-butyl chlorocarbonate in 500 ml. of methylene chloride, and the mixture was reacted in the same manner as in Example 10. After the reaction, the reaction liquid was washed and dried in the same manner as in Example 10, freed from the solvent by distillation and then subjected to recrystallization to obtain n-butyl 4,6-dimethyl-pyrimidyl-2-thiolcarbonate in a high yield.

EXAMPLE 12

Synthesis of benzyl 4,6-dimethyl-pyrimidyl-2-thiolcarbonate:

70.1 Grams (0.5 mole) of 2-mercapto-4,6-dimethyl-pyrimidine was added to 56.1 g. of a 50 % aqueous potassium hydroxide solution. Into the resulting mixture was dropped under stirring and ice-cooling a solution of 85.3 g. (0.5 mole) of carbobenzoxy chloride in 500 ml. of methylene chloride, and then the mixture was reacted at room temperature for 24 hours. After the reaction, the methylene chloride phase was separated, washed twice with 50 ml. of a saturated sodium bicarbonate solution and twice with 50 ml. of a 10 % aqueous sodium chloride solution, and dried over anhydrous sodium sulfate, and then the methylene chloride was concentrated to obtain 130 g. of crystalline benzyl 4,6-dimethyl-pyrimidyl-2-thiolcarbonate in yield of 94.9 %. When recrystallized from an ether-petroleum ether solvent, the product showed a melting point of 94° to 94.5°C.

Elementary analysis: Calcd.: C: 59.19 %, H: 5.30 %, N: 9.20 % (for $C_{14}H_{14}O_2N_2S$); Found: C: 58.98 %, H: 5.31 %, N: 9.22 %.

The infrared spectrum of the thus obtained compound is the same as shown in FIG. 5.

EXAMPLE 13

Synthesis of p-methoxybenzyl 4,6-dimethyl-pyrimidyl-2-thiolcarbonate:

Into a solution of 29 g. (0.29 mole) of phosgene in 100 ml. of methylene chloride was dropped under stirring at −30° to 10°C. a solution of 32.5 ml. (0.26 mole) of p-methoxybenzyl alcohol in 100 ml. of methylene chloride, and the mixed solution was further stirred for 30 minutes. Subsequently, nitrogen gas was injected to remove excess phosgene, and the resulting p-methoxybenzyloxy carbonyl chloride solution was mixed with 42.0 g. (0.3 mole) of 2-mercapto-4,6-dimethyl-pyrimidine. Into this mixture was dropped a sclution of 84 ml. (0.6 mole) of triethylamine in 100 ml. of methylene chloride. Thereafter, the temperature was gradually elevated to room temperature, and the mixture was reacted at room temperature for 4 hours. After the reaction, the methylene chloride was concentrated and then 200 ml. of ether and 100 ml. of water were added to the reaction liquid. Subsequently, the ether phase was separated, washed twice with 20 ml. of a cold 10 % aqueous citric acid solution and 20 ml. of a saturated aqueous sodium chloride solution and dried over anhydrous sodium sulfate, and then the ether was concentrated to obtain 70.5 g. of p-methoxybenzyl 4,6-dimethyl-pyrimidyl-2-thiolcarbonate in yield of 81.0 %. When recrystallized from an ether-petroleum ether solvent, the product showed a melting point of 58° to 60°C.

Elementary analysis: Calcd.: C: 59.19 %, H: 5.30 %, N: 9.20 % (for $C_{15}H_{16}O_3N_2S$); Found: C: 58.98 %, H: 5.31 %, N: 9.22 %.

The infrared spectrum of the thus obtained compound is the same as shown in FIG. 6.

EXAMPLE 14

Synthesis of p-chlorobenzyl 4,6-dimethyl-pyrimidyl-2-thiolcarbonate:

The p-chlorobenzyloxy carbonyl chloride solution prepared by the same procedure as in Example 13 was mixed with 0.3 mole of 2-mercapto-4,6-dimethyl-pyrimidine. Into the resulting mixture was dropped a solution of 0.6 mole of triethylamine in 100 ml. of methylene chloride, and then the mixture was reacted in the same manner as in Example 13. After the reaction, the reaction liquid was washed and dried in the same manner as in Example 13, concentrated and then recrystallized to obtain p-chlorobenzyl 4,6-dimethyl-pyrimidyl-2-thiolcarbonate in a high yield.

EXAMPLE 15

Synthesis of p-nitrobenzyl 4,6-dimethyl-pyrimidyl-2-thiolcarbonate:

The p-nitrobenzyloxy carbonyl chloride solution prepared by the same procedure as in Example 13 was mixed with 0.3 mole of 2-mercapto-4,6-dimethyl-pyrimidine. Into the resulting mixture was dropped a solution of 0.6 mole of triethylamine in 100 ml. of methylene chloride, and then the mixture was reacted in the same manner as in Example 13. After the reaction, the reaction liquid was washed and dried in the same manner as in Example 13, concentrated and then recrystallized to obtain p-nitrobenzyl 4,6-dimethyl-pyrimidyl-2-thiolcarbonate in a high yield.

Applications as acylating agents of the thiolcarbonates represented by the formula (I) are explained below with reference to examples.

EXAMPLE 16

Synthesis of N-t-butyloxycarbonyl-L-leucine:

6.56 Grams (0.050 mole) of L-leucine and 10.5 ml. (0.075 mole) of triethylamine were added to 27.5 ml. of water. To the resulting mixture was added a solution of 13.2 g. (0.055 mole) of t-butyl 4,6-dimethyl-pyrimidyl-2-thiolcarbonate in 27.5 ml. of dioxane, and then the mixture was reacted under stirring at room temperature for 10 hours. After completion of the reaction, 75 ml. of water was added to the reaction liquid, and unreacted thiolcarbonate was extracted thrice with 100 ml. of ethyl acetate. Subsequently, the aqueous phase was cooled to 0°C., adjusted to pH 3 by addition of a saturated aqueous citric acid solution, and then extracted once with 75 ml. of ethyl acetate and twice with 40 ml. of ethyl acetate. Thereafter, the ethyl acetate phases were united together, washed once with 50 ml. of an aqueous citric acid solution at pH 1 and twice with 50 ml. of a saturated aqueous sodium chloride solution and dried over anhydrous sodium sulfate, and then the ethyl acetate was removed by distillation under reduced pressure, whereby a syrupy residue was obtained. This residue was dissolved in 65 ml. of ethanol, and the resulting solution was charged with 50 ml. of water and then cooled to obtain 11.3 g. of crystals of N-t-butyloxycarbonyl-L-leucine monohydrate, yield 97.8 %, m.p. 69° to 74°C. [gradually melting at about 59°C.; Journal of American Chemical Society. 79, 6180 (1957): 67°–72°C.].

Elementary analysis: Calcd.: C: 52.99 %, H: 9.30 %, N: 5.62 %; Found: C: 52.88 %, H: 9.21 %, N: 5.68 %.

EXAMPLE 17

Example 16 was repeated, except that each of sodium hydroxide, triethylamine, sodium carbonate and sodium bicarbonate was used as the base; each of dioxane, t-butanol and dimethylformamide (D.M.F.) was used as the solvent; and the molar ratio (A.A/base) of base to L-leucine and the reaction temperature and time were varied as shown in Table 1. The yields of the resulting N-t-butyloxycarbonyl-L-leucine were as set forth in Table 1, provided that the yields are values of products prior to recrystallization.

Table 1

| Base | NaOH | | | | $N(C_2H_5)_3$ | | | | $Na_2CO_3$ | $NaHCO_3$ |
| --- | --- | --- | --- | --- | --- | --- | --- | --- | --- | --- |
| A.A./Base | 1.0/1.1 | 1.0/1.5 | 1.0/1.1 | | 1.0/1.5 | | | | 1.0/1.1 | 1.0/1.1 |
| Reaction temp. (°C.) | | 30–35 | | 30–35 | 15–20 | 30–35 | | 40–45 | 30–35 | 30–35 |
| Reaction time (hr.) | 2 | 5 | 10 | 10 | 10 | 5 | 10 | 2.5 | 10 | 10 |
| Solvent | | | | | | | | | | |
| Dioxane | 80.3% | 84.4% | 87.5% | 95.8% | 82.7% | — | 90.3% | 100% | 85.2% | 20.6% |
| t-Butanol | 74.4% | 86.1% | 86.4% | — | — | — | 86.5% | 96.8% | — | — |
| D.M.F. | — | 86.4% | 91.2% | — | — | 79.3% | 98.6% | 100% | 92.0% | — | — |

EXAMPLE 18

Synthesis of N-t-butyloxycarbonyl-L-alanine:

4.46 Grams (0.050 mole) of L-alanine and 10.5 ml. (0.075 mole) of triethylamine were added to 27.5 ml. of water. To the resulting mixture was added the same dioxane solution of t-butyl 4,6-dimethyl-pyrimidyl-2-thiolcarbonate as in Example 16, and the mixture was reacted under stirring at room temperature for 10 hours. After completion of the reaction, the reaction liquid was extracted, washed and dried in the same manner as in Example 16, and then the ethyl acetate was removed by distillation to obtain 9.38 g. of crystals of N-t-butyloxycarbonyl-L-alanine in yield of 99.2 %. When recrystallized from an ethyl acetate-petroleum ether solvent, the product showed a melting point of 81.0° to 82.0°C. [Journal of Chemical Society (C), 2632 (1967): 81° to 82°C.]

Elementary analysis: Calcd: C: 50.78 %, H: 7.99 %, N: 7.40 %; Found: C: 50.94 %, H: 7.82 %, N: 7.46 %.

EXAMPLE 19

Synthesis of dicyclohexylamine salt of N-t-butyloxycarbonyl-L-tyrosine:

9.05 Grams (0.050 mole) of L-tyrosine and 17.5 ml. (0.125 mole) of triethylamine were added to 27.5 ml. of water. To the resulting mixture was added the same dioxane solution of t-butyl 4,6-dimethyl-pyrimidyl-2-thiolcarbonate as in Example 16, and the mixture was reacted under stirring at room temperature for 24 hours. After completion of the reaction, the reaction liquid was extracted, washed and dried in the same manner as in Example 16. The thus treated liquid was added to a solution of 8.46 g. (0.050 mole) of dicyclohexylamine in 500 ml. of ethyl acetate, and the resulting mixture was allowed to stand overnight in a cold place, whereby crystals were deposited. The crystals were recovered by filtration and then washed with ethyl acetate to obtain 27.29 g. of a dicyclohexylamine salt of N-t-butyloxycarbonyl-L-tyrosine, yield 99.2 %, m.p. 208°C. (decomposition) [Journal of Chemical Society (C), 2632 (1967): 212°C.].

Elementary analysis: Calcd.: C: 67.50 %, H: 9.15 %, N: 6.05 %; Found: C: 67.47 %, H: 9.17 %, N: 5.98 %.

EXAMPLE 20

In the same manner as in the Example 18 or 19, various amino acids as shown in Table II were reacted with t-butyl 4,6-dimethyl-pyrimidyl-2-thiolcarbonate in the presence of triethylamine, and the reaction products were extracted and purified to obtain corresponding N-t-butyloxycarbonyl amino acids. Provided that in Run No. 3, ether was used as a precipitant for dicyclohexylamine salt. The results obtained were as set forth in Table II.

FIG. 8 – FIG. 11 show the infrared spectra of BOC-L-Ile-OH (monohydrate) (No. 2), BOC-L-Pro-OH (No. 4), BOC-L-Ser-OH (1/2 hydrate) (No. 5) and BOC-L-Val-OH (No. 7), shown in Table II, respectively.

Figure 8:
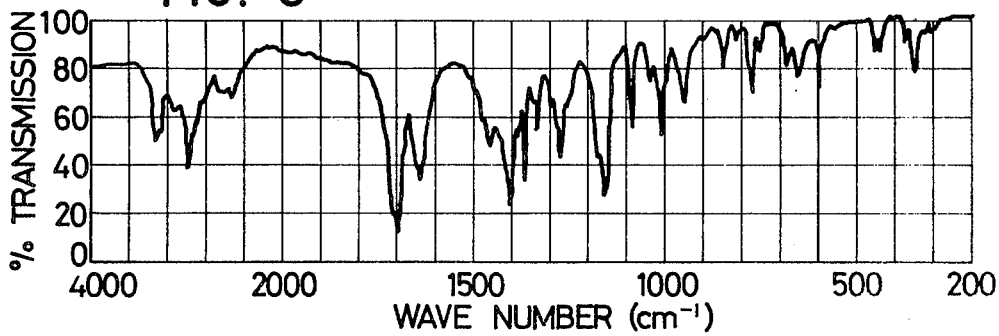
FIG. 8 – FIG. 22 are the infrared spectra of the acylated products obtained by using the thiolcarbonates of the formula (I) as acylating agents.

FIG. 8 shows the presence of —NH— (3300 cm⁻¹),

in the carboxyl group (1718 cm⁻¹) and

Figure 9:
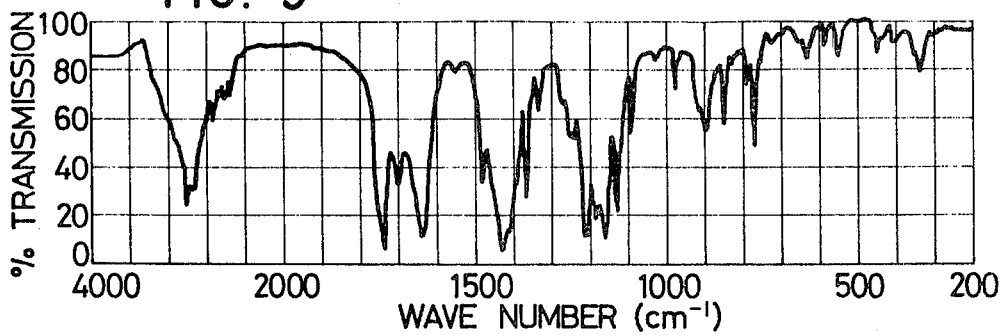

in the amide bond (1642 cm⁻¹).
FIG. 9 shows the presence of

in the carboxyl group (1737 cm⁻¹) and

in the

Figure 10:
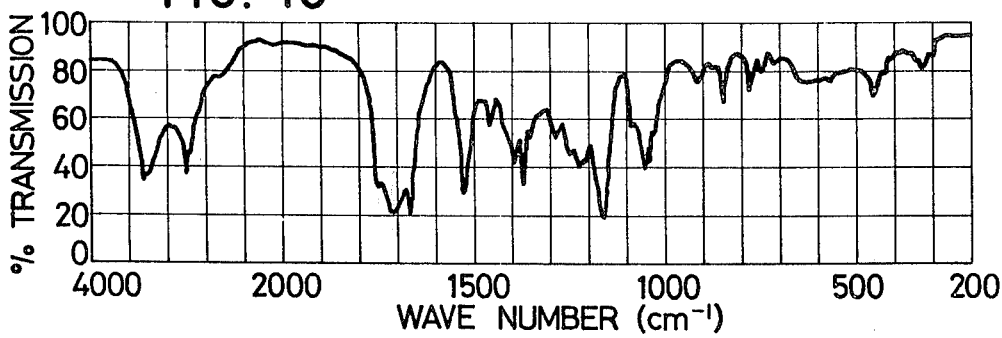

< bond (1638 cm⁻¹).
FIG. 10 shows the presence of —NH— (3452 cm⁻¹), —OH in the H₂O (3375 cm⁻¹, broad absorption),

in the carboxyl group (1708 cm⁻¹), and

Figure 11:
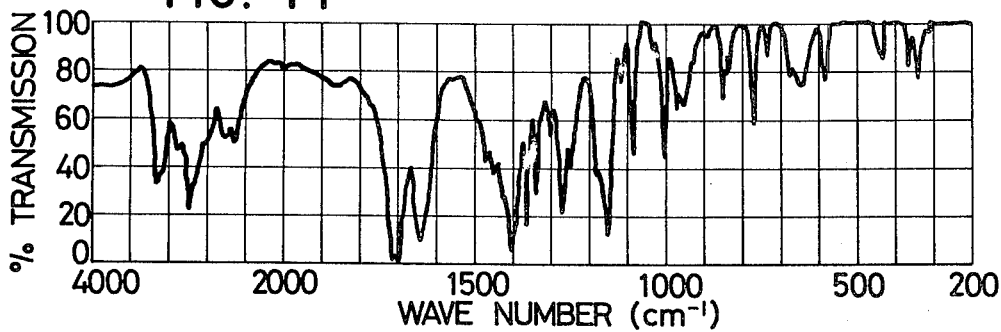

in the amide bond (1664 cm⁻¹).
FIG. 11 shows the presence of —NH— (3300 cm⁻¹),

in the carboxyl group (1705 cm⁻¹) and

in the amide bond (1645 cm⁻¹).

Table II

| Run No. | Amino acid | N-t-Butyloxy carbonyl amino acid | Yield (%) | Melting point (°C.) Present invention | Melting point (°C.) Literature value*[3] | Remarks |
|---|---|---|---|---|---|---|
| 1 | Gly-OH | BOC*[1]-Gly-OH | 92.0 | 87.0–89.0 | 94–95 | Process of Example 18 |
| 2 | L-Ile-OH | BOC-L-Ile-OH (monohydrate) | 100 | 68.0–71.0 | 66–68 | Process of Example 18 |
| 3 | L-Met-OH | BOC-L-Met-OH (DCHA*[2]) | 100 | 135.5–139.0 | 138–139 | Process of Example 19 |
| 4 | L-Pro-OH | BOC-L-Pro-OH | 95.5 | 136.0–137.0 | 134–136 | Process of Example 18 |
| 5 | L-Ser-OH | BOC-L-Ser-OH (1/2 hydrate) | 84.6 | 86.0–71.0 | 75–78 | Process of Example 18 |
| 6 | L-Trp-OH | BOC-L-Trp-OH | 100 | 137.0–138.0 | 135–137 | Process of Example 18 |

Table II-continued

| Run No. | Amino acid | N-t-Butyloxy carbonyl amino acid | Yield (%) | Melting point (°C.) Present invention | Melting point (°C.) Literature value[3] | Remarks |
|---|---|---|---|---|---|---|
| 7 | L-Val-OH | BOC-L-Val-OH | 98.6 | 76.5–78.6 | 72–73 | Process of Example 18 |

[1]BOC: t-Butyloxycarbonyl group 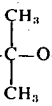

[2]DCHA: Dicyclohexylamine salt
[3]Literature: Liebigs Annalen der Chemie, 702, 188, (1967).

EXAMPLE 21

Synthesis of dicyclohexylamine salt of N-t-amyloxycarbonyl-L-alanine:

4.46 Grams (0.050 mole) of L-alanine and 10.5 ml. (0.075 mole) of triethylamine were added to 27.5 ml. of water. To the resulting mixture was added a solution of 14.0 g. (0.055 mole) of t-amyl 4,6-dimethyl-pyrimidyl-2-thiolcarbonate in 27.5 ml. of dioxane, and the mixture was reacted under stirring at room temperature for 24 hours. After completion of the reaction, the reaction liquid was extracted, washed and dried in the same manner as in Example 16, and then charged with 8.46 g. (0.050 mole) of dicyclohexylamine and with petroleum ether to precipitate 18.25 g. of a dicyclohexylamine salt of N-t-amyloxycarbonyl-L-alanine in yield of 98.1 %. When recrystallized from an ether-petroleum ether solvent, the product showed a melting point of 125° to 127°C. [Bulletin of the Chemical Society of Japan, 38(9), 1522 (1965): 124°–126°C.].

Elementary analysis: Calcd.: C: 65.58 %, H: 10.48 %, N: 7.55 %; Found: C: 65.73 %, H: 10.35 %, N: 7.41 %.

EXAMPLE 22

Synthesis of dicyclohexylamine salt of N-t-amyloxycarbonyl-L-tyrosine:

9.05 Grams (0.05 mole) of L-tyrosine and 17.5 ml. (0.125 mole) of tirethylamine were added to 27.5 ml. of water. To the resulting mixture was added the same dioxane solution of t-amyl 4,6-dimethyl-pyrimidyl-2-thiolcarbonate as in Example 21, and the mixture was reacted in the same manner as in Example 21. After completion of the reaction, the reaction liquid was extracted, washed and dried in the same manner as in Example 16. The thus treated liquid was charged with a solution of 8.46 g. (0.050 mole) of dicyclohexylamine in 500 ml. of ethyl acetate and with petroleum ether, and the resulting mixture was allowed to stand in a cold place, whereby crystals were deposited. The crystals were recovered by filtration and then washed with ethyl acetate to obtain 23.88 g. of a dicyclohexylamine salt of N-t-amyloxycarbonyl-L-tyrosine, yield 98.7 %, m.p. 202°C. (decomposition).

Elementary analysis: Calcd.: C: 68.11 %, H: 9.30 %, N: 5.88 %; Found: C: 68.23 %, H: 9.28 %, N: 5.79 %.

EXAMPLE 23

Synthesis of N-carbobenzoxy-benzylamine:

To a solution of 1.07 g. (0.01 mole) of benzylamine in 10 ml. of ether was added at room temperature a solution of 2.74 g. (0.01 mole) of benzyl 4,6-dimethyl-pyrimidyl-2-thiocarbonate in 10 ml. of ether, and the mixed solution was reacted under stirring for 30 minutes. With progress of the reaction, 2-mercapto-4,6-dimethylpyrimidine was liberated to form a precipitate. the precipitate was separated by filtration, and the filtrate was washed twice with 10 ml. of a 1N aqueous hydrochloric acid solution and 10 ml. of a 10 % aqueous sodium chloride solution and dried over anhydrous sodium sulfate, and then the ether was concentrated to obtain crystalline N-carbobenzoxy-benzylamine quantitatively. When recrystallized from an ether-petroleum ether solvent, the product showed a melting point of 61° to 62°C.

Elementary analysis: Calcd.: C: 74.67 %, H: 6.27 %, N: 5.80 %; Found: C: 74.48 %, H: 6.30 %, N: 5.78 %.

EXAMPLE 24

Synthesis of N-carbobenzoxy-L-tryptophan:

2.04 Grams (0.01 mole) of L-tryptophan and 1.67 g. (0.012 mole) of triethylamine were added to 8 ml. of water. To the resulting mixture was added a solution of 3.01 g. (0.011 mole) of benzyl 4,6-dimethyl-pyrimidyl-2-thiolcarbonate in 16 ml. of dioxane, and the mixture was reacted under stirring at 60° to 65°C. for 2 hours. After completion of the reaction, the dioxane was removed by distillation under reduced pressure, and 15 ml. of water was added to the residue. Thereafter, the unreacted thiolcarbonate was extracted with ethyl acetate, and the aqueous phase was adjusted to pH 3 by addition of a saturated aqueous citric acid solution, and then extracted once with 15 ml. of ethyl acetate and twice with 8 ml. of ethyl acetate. Subsequently, the ethyl acetate phases were united together, washed once with 10 ml. of a 1N aqueous hydrochloric acid solution and twice with 10 ml. of a saturated aqueous sodium chloride solution and dried over anhydrous sodium sulfate, and then the ethyl acetate was removed by distillation under reduced pressure, whereby crystals of N-carbobenzoxy-L-tryptophan were obtained substantially quantitatively. When recrystallized from an ether-petroleum ether solvent, the product showed a melting point of 122° to 124°C.

Elementary analysis: Calcd.: C: 67.59 %, H: 5.40 %, N: 8.15 %; Found: C: 67.45 %, H: 5.36 %, N: 8.28 %.

EXAMPLE 25

Synthesis of N-p-methoxybenzyloxycarbonyl-L-alanine:

8.9 Grams (0.1 mole) of L-alanine and 21 ml. (0.15 mole) of triethylamine were added to 55 ml. of water. To the resulting mixture was added a solution of 33.5 g. (0.11 mole) of p-methoxybenzyl 4,6-dimethylpyrimidyl-2-thiolcarbonate in 55 ml. of dioxane, and the mixture was reacted under stirring at room temperature for 10 hours. After completion of the reaction, the reaction liquid was charged with 150 ml. of water and then extracted thrice with 200 ml. of ethyl acetate to remove unreacted thiolcarbonate. Thereafter, the aqueous phase was cooled to 0°C., adjusted to pH 3 by addition of a 10 % aqueous citric acid solution and then extracted once with 150 ml. of ethyl acetate and twice with 80 ml. of ethyl acetate. Subsequently, the ethyl acetate phases were united together, washed twice with 100 ml. of a 10 % aqueous citric acid solution and twice with 100 ml. of water and dried over anhydrous sodium sulfate to obtain 24.3 g. of crystalline N-p-methoxybenzyloxycarbonyl-L-alanine in yield of 95.7 %. When recrystallized from an ethyl acetate-petroleum ether solvent, the product showed a melting point of 80° to 81.5°C. and specific rotation $[\alpha]_D^{20}$ of $-12.2$ (C = 3, acetic acid).

For comparison, N-p-methoxybenzoxycarbonyl-L-alanine was synthesized by acylating L-alanine with known acylating agents. The results obtained were as set forth in Table III.

in the carboxyl group (1710 cm$^{-1}$) and

in the amide bond (1685 cm$^{-1}$).

From Table III, it is clear that when the known acylating agents are used, L-alanine is required to be reacted over a long period of time, and the yields are relatively low even though L-alanine is reacted for such long period of time. Further, pMZ-Cl is readily decomposed, and therefore the reaction using said acylating agent should be effected at a low temperature.

EXAMPLE 26

In the same manner as in Example 25, the amino acids as shown in Table IV were reacted with p-methoxybenzyl 4,6-dimethyl-pyrimidyl-2-thiolcarbonate and the reaction products were purified to synthesize corresponding N-p-methoxybenzyloxycarbonyl amino acids. The yields and properties of the products obtained were as set forth in Table IV.

Table III

| Acylating agent | Reaction temperature (°C.) | Reaction time (hr.) | Yield of pMZ-L-Ala-OH | Literature |
|---|---|---|---|---|
| *1) 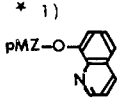 | Room temperature | 48 | 81 | Chem. Pham. Bull., 18, 2574 (1970) |
| 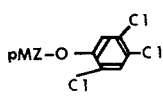 | "  <br> 50 | "  <br> 12 | 58  <br> 79 | "  <br> Ann. 724, 204 (1969) |
| 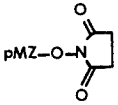 | Room temperature | 48 | 51 | ibid |
| 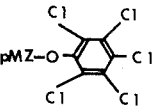 | " | " | 72 | " |
| 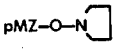 | " | 72 | 58 | Chem. & Ind. 1722 (1966) |
| pMZ-N$_3$ | " | 40 | 59 | Ber. 95, 1 (1962) |
| pMZ-Cl | 0-5 | 2 | 69.4 | Bull. Chem. Soc. Japan, 43, 177 (1970) |

*1)pMZ: p-Methoxybenzyloxycarbonyl group (CH$_3$O—⟨⟩—CH$_2$—O—C(=O)—)

Figure 12:
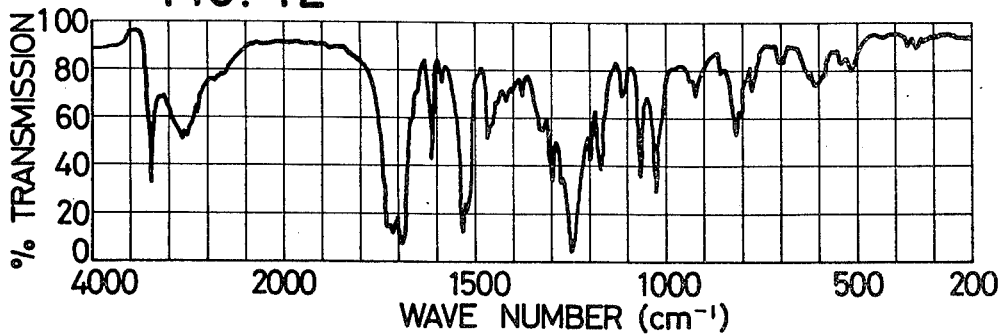

FIG. 12 shows the infrared spectrum of N-p-methoxybenzyloxycarbonyl-L-analine. The infrared spectrum shows the presence of —NH— (3350 cm$^{-1}$),

Table IV

| Run No. | Amino acid | pMZ-amino acid | Yield (%) | Melting point (°C.) | Specific rotation $[\alpha]_D^{20}$ |
|---|---|---|---|---|---|
| 1 | L-Asp-OH | pMZ-L-Asp-OH | 82.3 | 125–127 | +8.5 (C=1, acetic acid) |
| 2 | L-Ile-OH | pMZ-L-Ile-OH | 95.3 | 63–65 | +7.0 (C=2, ethanol) |
| 3 | L-Glu-OH | pMZ-L-Glu-OH | 100 | 107–110 | −7.1 (C=2, acetic acid) |
| 4 | Gly-OH | pMZ-Gly-OH | 100 | 96–98 | — |
| 5 | L-Met-OH | pMZ-L-Met-OH | 99.5 | 74–75 | −21.0 (C=0.9, methanol) |
| 6 | L-Phe-OH | pMZ-L-Phe-OH | 93.3 | 88–89.5 | +6.4 (C=2, acetic acid) |
| 7 | L-Ser-OH | pMZ-L-Ser-OH | 82.6 | 98–100 | +6.7 (C=0.856, acetic acid) |
| 8 | L-Val-OH | pMZ-L-Val-OH | 99.3 | 62.5–64.5 | +5.8 (C=1, D.M.F) |

FIG. 13 to FIG. 16 show the infrared spectra of pMZ-L-Asp-OH (No. 1), pMZ-L-Glu-OH (No. 3), pMZ-Gly-OH (No. 4) and pMZ-L-Ser-OH (No. 7), shown in Table IV, respectively.

Figure 13:
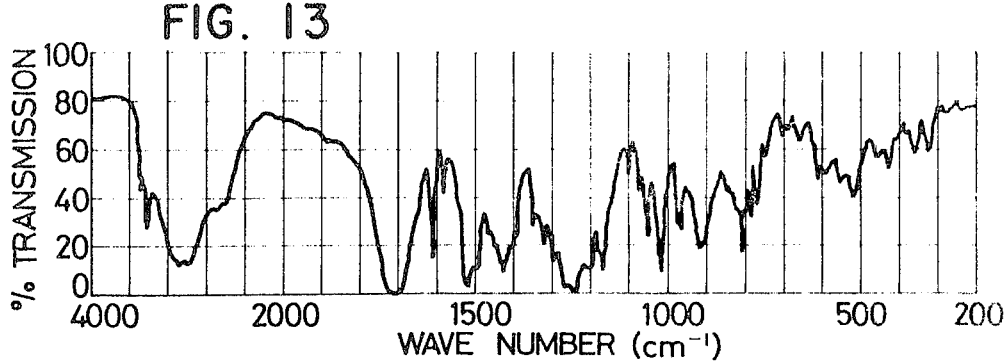

FIG. 13 shows the presence of —NH— (3375 cm$^{-1}$) and

in the carboxyl group and the amide bond (1705 cm$^{-1}$, broad absorption).

Figure 14:
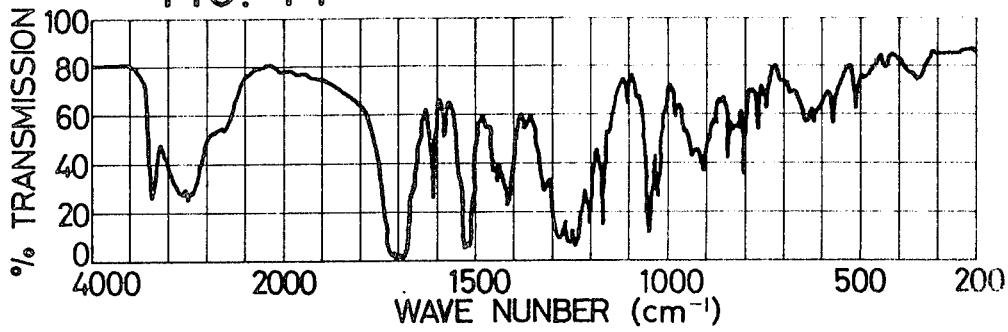

FIG. 14 shows the presence of —NH— (3300 cm$^{-1}$) and

in the carboxyl group and the amide bond (1688 cm$^{-1}$, broad absorption).

Figure 15:
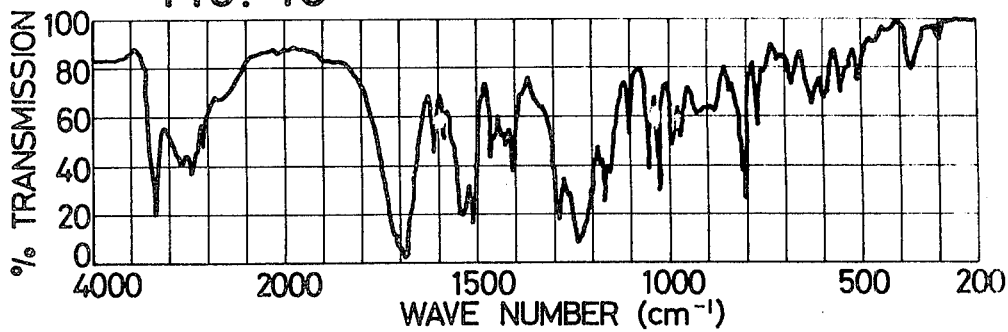

FIG. 15 shows the presence of —NH— (3300 cm$^{-1}$) and

in the carboxyl group and the amide bond (1688 cm$^{-1}$, broad absorption).

Figure 16:
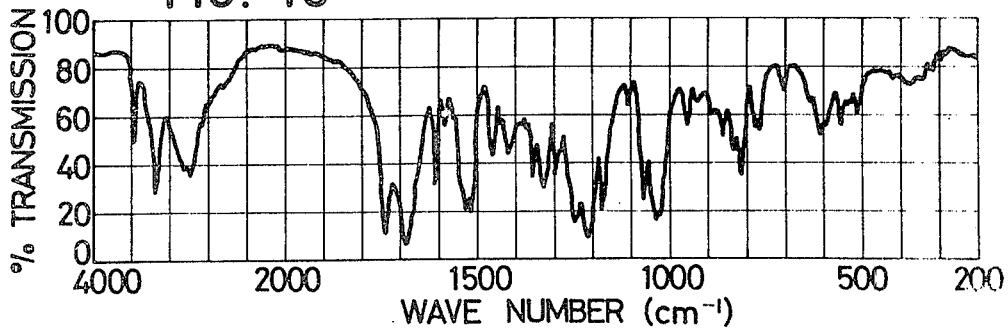

FIG. 16 shows the presence of -OH group (3550 cm$^{-1}$), —NH— (3325 cm$^{-1}$),

in the carboxyl group (1735 cm$^{-1}$) and

in the amide bond (1685 cm$^{-1}$).

EXAMPLE 27

Synthesis of N-p-methoxybenzyloxycarbonyl-L-asparagine:

In the same manner as in Example 25, 0.1 mole of L-asparagine was reacted with 0.11 mole of p-methoxybenzyl 4,6-dimethyl-pyrimidyl-2-thiolcarbonate. The reaction liquid was charged with 150 ml. of water and then extracted thrice with 200 ml. of ethyl acetate to remove unreacted thiolcarbonate. Subsequently, the aqueous phase was cooled to 0°C., adjusted to pH 3 by addition of a saturated aqueous citric acid solution and then allowed to stand for one day in a cold place, whereby crystals were deposited. The crystals were recovered by filtration and then dried to obtain 24.5 g. of N-p-methoxybenzyloxycarbonyl-L-asparagine, yield 82.3 %, m.p. 160° - 163°C., $[\alpha]_D^{20}$ = −5.0 (C = 1, methanol).

Figure 17:
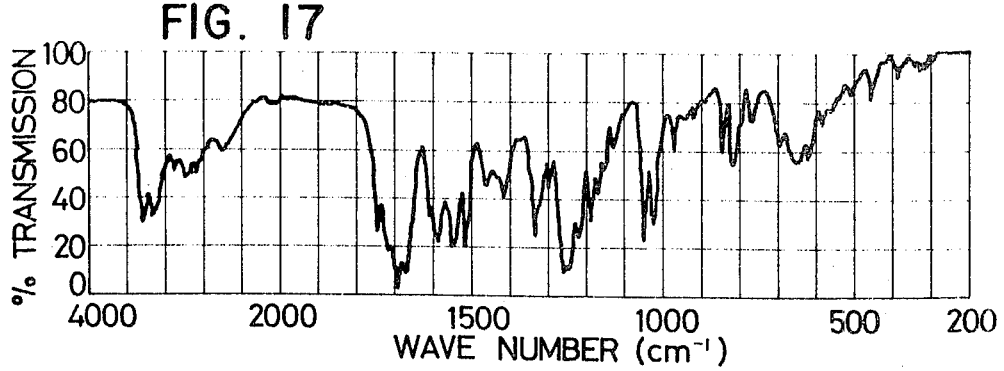

FIG. 17 shows the infrared spectrum of N-p-methoxybenzyloxycarbonyl-L-asparagine. The infrared spectrum shows the presence of —NH$_2$ group (3375 cm$^{-1}$), —NH— (3280 cm$^{-1}$),

in the carboxyl group (1743 cm$^{-1}$),

in the amide bond (1690 cm$^{-1}$) and

in the acid amide group (1670 cm$^{-1}$).

EXAMPLE 28

Synthesis of dicyclohexylamine salt of N-p-methoxybenzyloxycarbonyl-L-leucine:

In the same manner as in Example 25, 0.1 mole of L-leucine was reacted with 0.11 mole of p-methoxy benzyl 4,6-dimethyl-pyrimidyl-2-thiolcarbonate, and the reaction product was purified to obtain 29.6 g. of syrupy N-p-methoxybenzyloxycarbonyl-L-leucine in yield of 99.2%. The thus obtained N-p-methoxybenzyloxycarbonyl-L-leucine was dissolved in 300 ml. of ethyl acetate, and a solution of 18.1 g. of dicyclohexylamine in 200 ml. of acetic acid was added to the resulting solution. Subsequently, the mixed solution was allowed to stand, whereby a dicyclohexylamine salt of said N-p-methoxybenzyloxycarbonyl-L-leucine was deposited as a precipitate. When recovered by filtration and dried, the said salt showed a melting point of 156° to 160°C. and a specific rotation $[\alpha]_D^{20}$ of −6.9 (C = 2, methanol).

EXAMPLE 29

Synthesis of dicyclohexylamine salt of N-p-methoxybenzyloxycarbonyl-L-proline:

In the same manner as in Example 25, 0.1 mole of L-proline was reacted with 0.11 mole of p-methoxybenzyl 4,6-dimethyl-pyrimidyl-2-thiolcarbonate, and the reaction product was purified to obtain 27.5 g. of syrupy N-p-methoxybenzyloxycarbonyl-L-proline in yield of 98.6 %. The thus obtained N-p-methoxybenzyloxycarbonyl-L-proline was treated in the same manner as in Example 28 to obtain a dicyclohexylamine salt thereof, m.p. 145° – 147°C., $[\alpha]_D^{20} = -23.7$ ($C = 1$, methanol).

EXAMPLE 30

Synthesis of N-benzhydrylaurbonyl glycine:

0.7506 Gram (0.01 mole) of glycine and 2.1 ml. (0.015 mole) of triethylamine were added to 5.5 ml. of water. To the resulting mixture was added a solution of 3.8549 g. (0.011 mole) of benzhydroxy 4,6-dimethyl-pyrimidyl-2-thiocarbonate in 11 ml. of dioxane, and the mixture was reacted overnight under stirring at room temperature. After completion of the reaction, the reaction liquid was charged with 50 ml. of water and washed twice with 30 ml. of ethyl acetate. Subsequently, the aqueous phase was adjusted, under cooling to 0°C., to pH 2 by addition of 15 ml. of a cold 5N aqueous hydrochloric acid solution, and then extracted once with 30 ml. of ethyl acetate and twice with 15 ml. of ethyl acetate. Thereafter, the ethyl acetate phases were united together, washed twice with 15 ml. of a cold aqueous hydrochloric acid solution and twice with 30 ml. of a saturated aqueous sodium chloride solution, and dried over anhydrous sodium sulfate, and then the ethyl acetate was removed by distillation to obtain 2.731 g. of crude N-benzhydroxycarbonyl glycine in yield of 95.7 %. When recrystallized from an ether-petroleum ether solvent, the product showed a melting point of 113° to 113°C.

Elementary analysis: Calcd.: C: 67.36 %, H: 5.30 %, N: 4.91 %; Found: C: 67.46 %, H: 5.41 %, N: 4.77 %.

Figure 18:
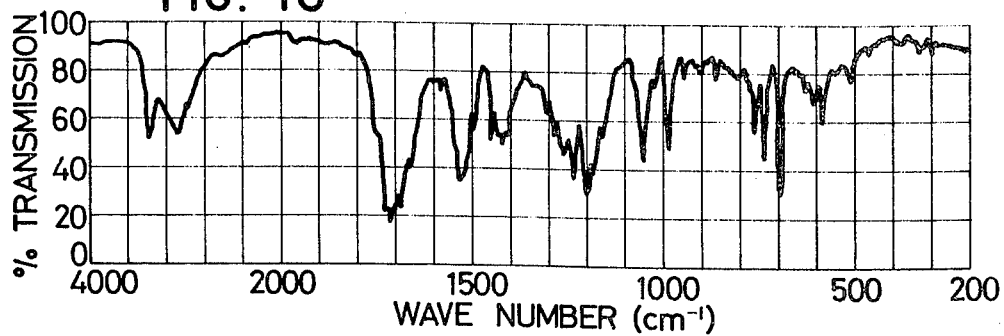

FIG. 18 shows the infrared spectrum of N-benzhydroxycarbonyl glycine. The infrared spectrum shows the presence of —NH— (3330 cm⁻¹), $$-\overset{O}{\underset{\|}{C}}-$$

in the carboxyl group (1710 cm⁻¹) and $$-\overset{O}{\underset{\|}{C}}-$$

in the amide bond (1660 cm⁻¹).

EXAMPLE 31

In the same manner as in Example 30, the amino acids as shown in Table V were reacted with benzhydryl 4,6-dimethyl-pyrimidyl-2-thiolcarbonate and the reaction products were purified to obtain corresponding N-benzhydroxycarbonyl amino acids. The results obtained were as set forth in Table V. The dicyclohexylamine salts in Run Nos. 1, 2 and 4 were prepared in the manner mentioned previously.

Table V

| Run No. | L-Amino acid | BhOC-L-amino acid*[1] | Yield (%) | Melting point (°C.) | Specific rotation $[\alpha]_D^{20}$ | | Elementary analysis (%) | | |
|---|---|---|---|---|---|---|---|---|---|
| | | | | | | | C | H | N |
| 1 | L-Ala-OH | BhOC-L-Ala-OH.DCHA*[2] | 84.0 | 162–164 | +9.1 (C=0.33, (chloroform) | Calcd. Found | 72.74 72.00 | 8.39 8.44 | 5.83 5.51 |
| 2 | L-Phe-OH | BhOC-L-Phe-OH.DCHA | 87.4 | 168–171 | +59.0 (C=0.40, (chloroform) | Calcd. Found | 75.51 75.61 | 7.98 8.01 | 5.04 5.05 |
| 3 | L-Pro-OH | BhOC-L-Pro-OH*[3] | 90.5 | 81–83 | −55.6 (C=1 acetic acid) | Calcd. Found | 70.14 69.73 | 5.89 6.02 | 4.30 4.09 |
| 4 | L-Val-OH | BhOC-L-Val-OH.DCHA | 96.2 | 137–140 | +9.5 (C=0.40, chloroform | Calcd. Found | 73.19 73.03 | 8.72 8.79 | 5.51 5.34 |

*[1]BhOC: N-benzhydroxycarbonyl group $$\text{(}\underset{\text{Ph}}{\underset{\text{Ph}}{\bigcirc\bigcirc}}\text{CH}-\text{O}-\overset{O}{\underset{\|}{C}}-\text{)}$$

*[2]DCHA: Dicyclohexylamine salt (recrystallized from chloroform-acetone-ether).
*[3]Washed with ether-petroleum ether after crystallization.

FIG. 19 – FIG. 22 show the infrared spectra of BhOC-L-Ala-OH.DCHA (No. 1), BhOC-L-Phe-OH.DCHA (No. 2), BhOC-L-Pro-OH (No. 3) and BhOC-L-Val-OH.DCHA (No. 4), shown in Table V, respectively.

Figure 19:
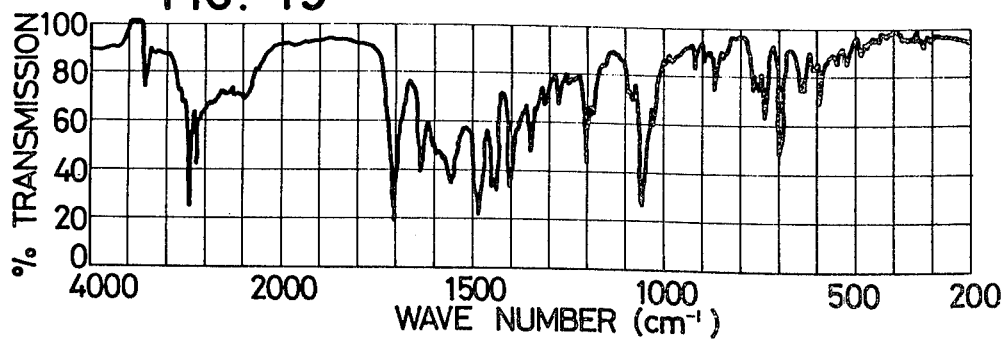

FIG. 19 shows the presence of —NH— (3380 cm⁻¹), $$-\overset{O}{\underset{\|}{C}}-$$

in the carboxyl group (1707 cm⁻¹) and $$-\overset{O}{\underset{\|}{C}}-$$

in the amide bond (1638 cm⁻¹).

Figure 20:
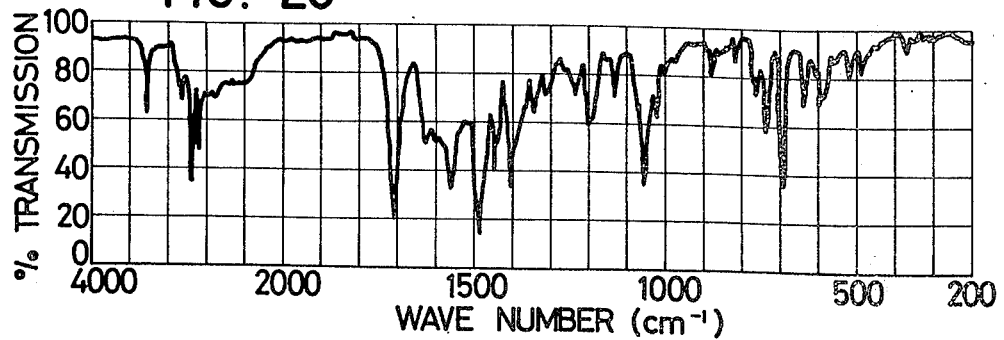

FIG. 20 shows the presence of —NH— (3400 cm⁻¹), $$-\overset{O}{\underset{\|}{C}}-$$

in the carboxyl group (1711 cm⁻¹) and in the amide bond (1630 cm$^{-1}$).

Figure 21:
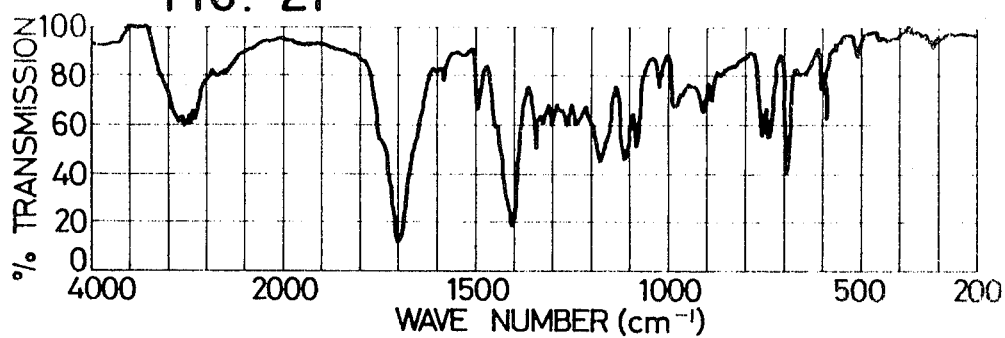

FIG. 21 shows the presence of

in the carboxyl group (1708 cm$^{-1}$) and

in the

< bond (1650 cm$^{-1}$, broad absorption).

Figure 22:
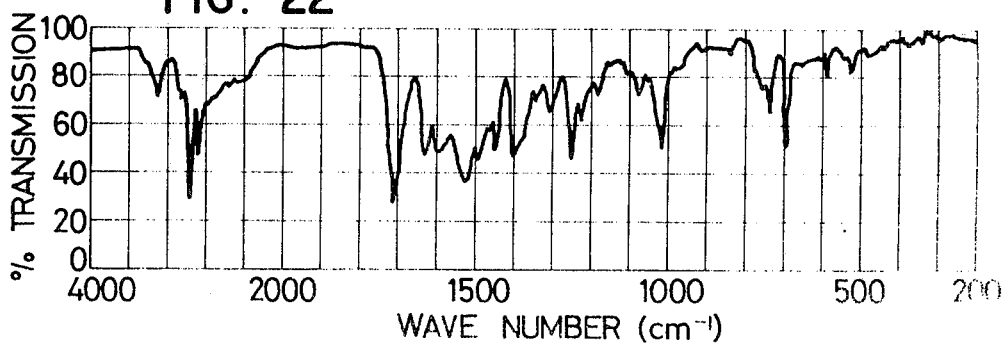

FIG. 22 shows the presence of —NH— (3280 cm$^{-1}$),

in the carboxyl group (1701 cm$^{-1}$) and

in the amide bond (1630 cm$^{-1}$).

EXAMPLE 32

0.01 Mole of each of the thiolcarbonates as shown in Table VI was dissolved in 30 ml. of ethyl acetate. To the resulting solution was added a solution of 0.02 mole of phenylhydrazine or benzylamine in 20 ml. of ethyl acetate, and the mixed solution was reacted for one day under stirring. The reaction liquid was suction-filtered, and the filtrate was washed twice with a cold 5 % aqueous hydrochloric acid solution and twice with 30 ml. of a saturated aqueous sodium chloride solution and dried over anhydrous sodium sulfate, and then the ethyl acetate was removed by distillation to synthesize a corresponding N-acylamine. The results obtained were as set forth in Table VI.

Table VI

| Run No. | Thiocarbonate | Amine | Product (N-acylamine) |
|---|---|---|---|
| 1 | BOC-S-(4,6-dimethylpyrimidin-2-yl) | Phenylhydrazine | BOC-HNHN—⌬ |
| 2 | | Benzylamine | BOC-HNH₂C—⌬ |
| 3 | pMZ-S-(4,6-dimethylpyrimidin-2-yl) | Phenylhydrazine | pMZ-HNHN—⌬ |
| 4 | | Benzylamine | pMZ-HNH₂C—⌬ |
| 5 | BhOC-S-(4,6-dimethylpyrimidin-2-yl) | Phenylhydrazine | BhOC-HNHN—⌬ |
| 6 | | Benzylamine | BhOC-HNH₂C—⌬ |

| Yield (%) | Recrystallization solvent | Melting point (°C.) | Elementary analysis (%) | | | |
|---|---|---|---|---|---|---|
| | | | | C | H | N |
| 90.3 | Ether/Petroleum ether | 89–91 | Calcd. | 63.44 | 7.74 | 13.45 |
| | | | Found | 63.74 | 7.81 | — |
| 95.6 | n-Hexane/n-Heptane | 55–56 | Calcd. | 69.53 | 8.27 | 6.76 |
| | | | Found | 69.75 | 8.29 | 6.70 |
| 94.7 | Ethyl acetate/Petroleum ether | 95–96 | Calcd. | 66.16 | 5.92 | 10.29 |
| | | | Found | 65.99 | 5.92 | — |
| 95.3 | '' | 75.5–76.5 | Calcd. | 70.83 | 6.32 | 5.16 |
| | | | Found | 71.09 | 6.17 | 4.96 |
| 93.9 | '' | 103–104 | Calcd. | 75.45 | 5.70 | 8.80 |
| | | | Found | 74.19 | 5.81 | — |
| 99.6 | '' | 103–104 | Calcd. | 79.47 | 6.03 | 4.41 |
| | | | Found | 79.61 | 6.10 | 4.32 |

What is claimed is:

1. A process for producing a thiolcarbonate represented by the formula,

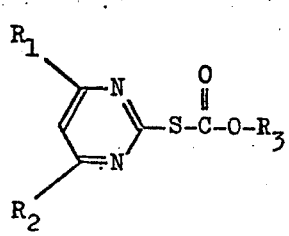

wherein $R_1$ and $R_2$ are individually hydrogen or methyl, and $R_3$ is a straight chain or branched chain alkyl having 1 to 5 carbons, a straight chain or branched chain alkenyl having 2 to 5 carbon, or a benzyl or diphenylmethyl which may be nuclear substituted, which comprises reacting a 2-mercapto-4- and/or 6-methyl-substituted or unsubstituted pyrimidine represented by the formula,

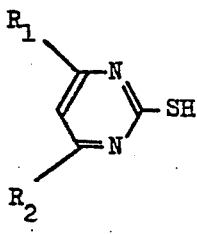

wherein $R_1$ and $R_2$ are as defined above, with an alkali metal hydroxide in an aqueous solution to form an alkali metal salt of the formula,

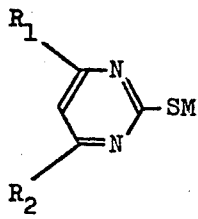

wherein $R_1$ and $R_2$ are as defined above, and M is an alkali metal, reacting the thus formed alkali metal salt (II) with phosgene in an inert solvent in the absence of water at a temperature below the reflux temperature of said solvent to prepare a pyrimidyl-2-thiolchloroformate of the formula,

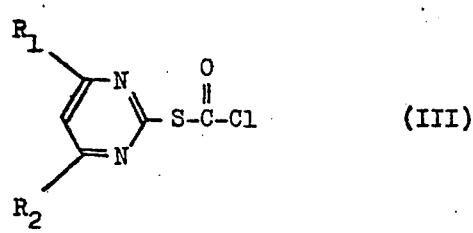

wherein $R_1$ and $R_2$ are as defined above, and
then reacting the compound of the formula (III) with an alcohol represented by the formula, $$R_3 - OH \quad (IV)$$

wherein $R_3$ is as defined above, in an inert solvent in the presence of a base and in the absence of water at a temperature below the reflux temperature of the solvent used.

2. A process according to claim 1, wherein the pyrimidyl-2-thiolchloroformate represented by the formula (III) is reacted with the alcohol represented by the formula (IV) at about room temperature.

3. A process according to claim 1, wherein the alkali metal salt represented by the formula (II) is reacted with phosgene at a temperature within the range from 0° to 40°C.

4. A process according to claim 1, wherein the alkali metal salt represented by the formula (II) is reacted with phosgene in an amount of 1 to 2 moles per mole of the alkali metal salt.

5. A process according to claim 1, wherein the alkali metal salt represented by the formula (II) is reacted with phosgene in an inert solvent selected from the group consisting of petroleum ether, benzene, toluene, methylene chloride, xylene, chloroform and tetrahydrofuran.

6. A process according to claim 1, wherein the alcohol represented by the formula (IV) is selected from the group consisting of methanol, ethanol, n-propanol, iso-propanol, allyl alcohol, n-butanol, t-butanol, amyl alcohol, t-amyl alcohol, benzyl alcohol, anise alcohol, 2,4-dimethoxybenzyl alcohol, 2,4,6-trimethoxybenzyl alcohol, p-nitrobenzyl alcohol, p-chlorobenzyl alcohol, p-bromobenzyl alcohol and benzhydrol.

7. A process according to claim 1, wherein the reaction of the pyrimidyl-2-thiolchloroformate represented by the formula (III) with the alcohol represented by the formula (IV) is effected by using as the base or as the base and inert solvent a tertiary amine.

8. A process according to claim 7, wherein the tertiary amine is triethylamine, N-alkylmorpholine, N,N-dialkylaniline, pyridine or quinoline.

9. A process according to claim 1, wherein the reaction of the pyrimidyl-2-thiolchloroformate with the alcohol represented by the formula (IV) is effected by using as the inert solvent one member selected from the group consisting of ether, benzene, petroleum ether, toluene, xylene, methylene chloride, chloroform, petroleum benzene and tetrahydrofuran.

* * * * *

UNITED STATES PATENT OFFICE
CERTIFICATE OF CORRECTION

Patent No. __3,936,452__          Dated __February 3, 1976__

Inventor(s) __Takeshi NAGASAWA; Katumasa KUROIWA and Kouichi NARITA__

It is certified that error appears in the above-identified patent and that said Letters Patent are hereby corrected as shown below:

After Item [62] insert:

[30]      FOREIGN APPLICATION PRIORITY DATA

Sept. 17, 1971  Japan................46-72261
      Sept. 27, 1971  Japan................46-75306
      Sept. 30, 1971  Japan................46-76555
      Jan. 10, 1972  Japan................ 47-5116

Signed and Sealed this eighteenth Day of May 1976

[SEAL]

Attest:

RUTH C. MASON
*Attesting Officer*

C. MARSHALL DANN
*Commissioner of Patents and Trademarks*